(12) United States Patent
Tsur et al.

(10) Patent No.: US 11,712,248 B2
(45) Date of Patent: Aug. 1, 2023

(54) DELAYING PRE-TERM BIRTH

(71) Applicants: Tel HaShomer Medical Research Infrastructure and Services Ltd., Ramat-Gan (IL); The Trendlines Group Ltd., Misgav (IL)

(72) Inventors: Abraham Tsur, Ramat-Gan (IL); Sharon Farber, Nofit (IL); Roy Mashiach, Ramat-Gan (IL); Yosef Hazan, Haifa (IL); David Shashar, Shoham (IL); Avshalom Shenhav, Haifa (IL)

(73) Assignees: Tel HaShomer Medical Research Infrastructure and Services Ltd., Ramat-Gan (IL); The Trendlines Group Ltd., Misgav (IL)

( * ) Notice: Subject to any disclaimer, the term of this patent is extended or adjusted under 35 U.S.C. 154(b) by 559 days.

(21) Appl. No.: 16/706,986

(22) Filed: Dec. 9, 2019

(65) Prior Publication Data
US 2020/0129179 A1 Apr. 30, 2020

Related U.S. Application Data

(63) Continuation of application No. 15/302,190, filed as application No. PCT/IL2015/050402 on Apr. 14, 2015, now Pat. No. 10,499,926.
(Continued)

(51) Int. Cl.
*A61B 17/42* (2006.01)
*A61B 17/122* (2006.01)
(Continued)

(52) U.S. Cl.
CPC .......... *A61B 17/122* (2013.01); *A61B 5/4356* (2013.01); *A61B 5/6846* (2013.01);
(Continued)

(58) Field of Classification Search
CPC ... A61B 17/42; A61B 17/122; A61B 17/4241; A61B 17/1227; A61B 5/4356; A61B 5/6847; A61M 31/00
See application file for complete search history.

(56) References Cited

U.S. PATENT DOCUMENTS

| 604,958 A | 5/1898 | Biesmeyer |
| 804,086 A | 11/1905 | Barchfeld et al. |
(Continued)

FOREIGN PATENT DOCUMENTS

| CN | 202365885 | 8/2012 |
| CN | 202458542 | 10/2012 |
(Continued)

OTHER PUBLICATIONS

Supplementary Partial European Search Report and the Provisional Opinion dated Feb. 15, 2022 From the European Patent Office Re. Application No. 19822823.1. (20 Pages).
(Continued)

*Primary Examiner* — Vi X Nguyen

(57) ABSTRACT

A device for retarding birth including an upper ring for surrounding a cervix, an anchoring component for anchoring the device, and an elastic component for attaching the upper ring to the anchoring component, wherein the elastic component pushes the upper ring and the anchoring component apart. A device for retarding birth including a sleeve for surrounding a cervix along a greater portion of a length of the cervix, a support strip on the sleeve directed along an axis of the sleeve, and a ring at least partially around the sleeve, in which when a top of the sleeve is pushed to expand radially, the support strip pivots on the ring, such that an end of the support strip near the top of the sleeve moves radially
(Continued)

outward, and an end of the support strip near the bottom of the sleeve moves radially inward. Related apparatus and methods are also described.

23 Claims, 26 Drawing Sheets

Related U.S. Application Data

(60) Provisional application No. 61/979,006, filed on Apr. 14, 2014.

(51) Int. Cl.
    *A61B 5/00*         (2006.01)
    *A61F 6/08*         (2006.01)
    *A61M 31/00*      (2006.01)
    *A61B 90/00*        (2016.01)
    *A61B 17/00*        (2006.01)

(52) U.S. Cl.
    CPC .......... *A61B 5/6847* (2013.01); *A61B 5/6882* (2013.01); *A61B 5/6885* (2013.01); *A61B 17/1227* (2013.01); *A61B 17/42* (2013.01); *A61F 6/08* (2013.01); *A61M 31/00* (2013.01); *A61B 5/435* (2013.01); *A61B 2017/00221* (2013.01); *A61B 2017/00535* (2013.01); *A61B 2017/00734* (2013.01); *A61B 2017/00893* (2013.01); *A61B 2017/4225* (2013.01); *A61B 2090/065* (2016.02); *A61B 2090/0811* (2016.02)

(56) References Cited

U.S. PATENT DOCUMENTS

| | | | |
|---|---|---|---|
| 1,019,373 | A | 3/1912 | Shaulis |
| 1,083,721 | A | 1/1914 | Asch |
| 1,162,568 | A | 11/1915 | Carey |
| 1,219,496 | A | 3/1917 | Shaulis |
| 1,634,555 | A | 7/1927 | Peloubet |
| 2,618,261 | A | 11/1952 | Butts |
| 3,741,216 | A | 6/1973 | Yosowitz et al. |
| 5,807,281 | A | 9/1998 | Welch |
| 5,871,499 | A * | 2/1999 | Hahn ..................... A61B 17/42 |
| | | | 600/588 |
| 6,981,990 | B2 | 1/2006 | Keller |
| 8,550,088 | B1 * | 10/2013 | Booher, Sr. ........ A61B 17/4241 |
| | | | 128/846 |
| 2004/0092847 | A1 | 5/2004 | Welch |
| 2004/0153008 | A1 | 8/2004 | Sharf et al. |
| 2008/0171950 | A1 | 7/2008 | Franco |
| 2010/0228269 | A1 | 9/2010 | Garrison et al. |
| 2013/0053670 | A1 | 2/2013 | Aina-Mumuney et al. |
| 2013/0237766 | A1 * | 9/2013 | Pell ..................... A61B 5/0051 |
| | | | 600/211 |
| 2014/0073879 | A1 | 3/2014 | Cantor et al. |
| 2014/0276916 | A1 | 9/2014 | Ahluwalia et al. |
| 2017/0020529 | A1 | 1/2017 | Tsur et al. |
| 2019/0008674 | A1 | 1/2019 | Myers et al. |
| 2021/0236170 | A1 | 8/2021 | Shashar et al. |

FOREIGN PATENT DOCUMENTS

| | | |
|---|---|---|
| EP | 0084755 | 12/1982 |
| FR | 2455881 | 12/1980 |
| JP | H10-118048 | 5/1998 |
| TW | 201927265 | 7/2019 |
| WO | WO 01/01899 | 1/2001 |
| WO | WO 2010/021695 | 2/2010 |
| WO | WO 2010/114577 | 10/2010 |
| WO | WO 2011/103473 | 11/2011 |
| WO | WO 2014/164700 | 10/2014 |
| WO | WO 2015/159291 | 10/2015 |
| WO | WO 2019/244159 | 12/2019 |
| WO | WO 2019/244159 A8 | 2/2020 |
| WO | WO 2019/244159 A9 | 2/2021 |

OTHER PUBLICATIONS

Communication Pursuant to Article 94(3) EPC dated Feb. 18, 2020 From the European Patent Office Re. Application No. 15780710.8. (12 Pages).

Supplementary European Search Report and the European Search Opinion dated May 17, 2022 From the European Patent Office Re. Application No. 19822823.1. (13 Pages).

International Preliminary Report on Patentability dated Dec. 30, 2020 From the International Bureau of WIPO Re. Application No. PCT/IL2019/050696. (12 Pages).

Examination Report Under Sections 12 & 13 of the Patents Act, 1970 and the Patents Rules, dated Jan. 22, 2003 From the Government of India. Intellectual Property India, Patents, Designs, Trade Marks, Geographical Indications, The Patent Office Re. Application No. 201627035298. (5 Pages).

Communication Relating to the Results of the Partial International Search dated Jul. 28, 2015 From the International Searching Authority Re. Application No. PCT/IL2015/050402.

European Search Report and the European Search Opinion dated Nov. 15, 2017 From the European Patent Office Re. Application No. 15780710.8. (12 Pages).

International Preliminary Report on Patentability dated Oct. 27, 2016 From the International Bureau of WIPO Re. Application No. PCT/IL2015/050402. (9 Pages).

International Search Report and the Written Opinion dated Sep. 1, 2015 From the International Searching Authority Re. Application No. PCT/IL2015/050402.

International Search Report and the Written Opinion dated Nov. 14, 2019 From the International Searching Authority Re. Application No. PCT/IL2019/050696. (42 Pages).

Invitation to Pay Additional Fees and Communication Relating to the Results of the Partial International Search dated Sep. 26, 2019 From the International Searching Authority Re. Application No. PCT/IL2019/050696. (26 Pages).

Notice of Reason for Rejection dated Mar. 5, 2019 From the Japan Patent Office Re. Application No. 2014-513308 and Its Translation Into Enghsh.(12 Pages).

Notification of Office Action and Search Report dated Jun. 5, 2019 From the State Intellectual Property Office of the People's Republic of China Re. Application No. 201580031813.X. (5 Pages).

Notification of Office Action dated Sep. 4, 2018 From the State Intellectual Property Office of the People's Republic of China Re. Application No. 201580031813.X and Its Translation Into English. (4 Pages).

Official Action dated Feb. 7, 2019 From the US Patent and Trademark Office Re. U.S. Appl. No. 15/302,190. (15 pages).

Restriction Official Action dated Aug. 8, 2018 From the US Patent and Trademark Office Re. U.S. Appl. No. 15/302,190. (7 pages).

Translation of Notification dated Jun. 18, 2019 From OA dated Jun. 5, 2019 From the State Intellectual Property Office of the People's Republic of China Re. Application No. 201580031813.X. (2 Pages).

ACOG "Cerclage for the Management of Cervical Insufficiency", The American College of Obstetricians and Gynecologists, Clinical Management Guidelines for Obstetrician-Gynecologists, Practice Bulletin 142, 123(2 Pt. 1): 372-379, Feb. 2014.

ACOG "The Management of Preterm Labor", The American College of Obstetricians and Gynecologists, Clinical Management Guidelines for Obstetrician-Gynecologists, Practice Bulletin 127, 119(6): 1308-1317, Jun. 2012.

Lawn et al. "Global Report on Preterm Birth and Stillbirth (1 of 7): Definitions, Description of the Burden and Opportunities to Improve Data", BMC Pregnancy and Childbirth, 10(Suppl.1): S1-S22, 2010.

Verma et al. "Continuous Wireless Monitoring of the Cervical Dilation of a Pregnant Woman", IEEE International Workshop on Medical Measurements and Applications: 1-4, May 9-10, 2008.

(56) References Cited

OTHER PUBLICATIONS

Examination Report Under Sections 12 & 13 of the Patents Act, 1970 and the Patents Rules, 2003 dated Oct. 11, 2022 From the Government of India, Intellectual Property India, Patents, Designs, Trade Marks, Geographical Indications, The Patent Office Re. Application No. 202127002499. (6 Pages).

* cited by examiner

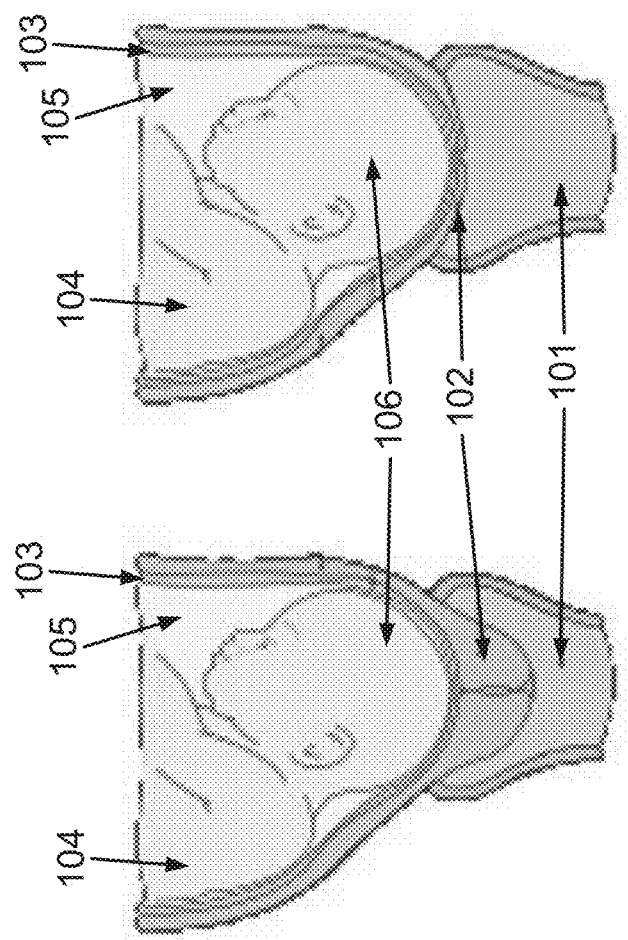

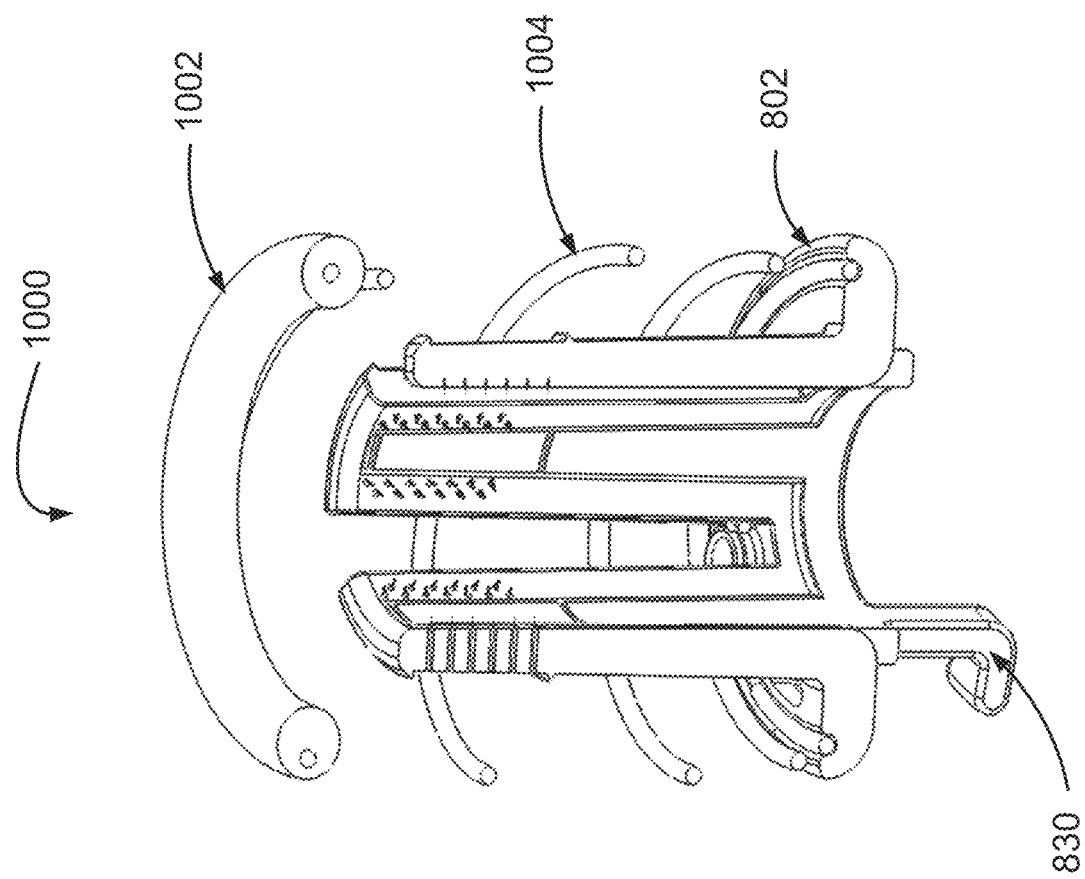
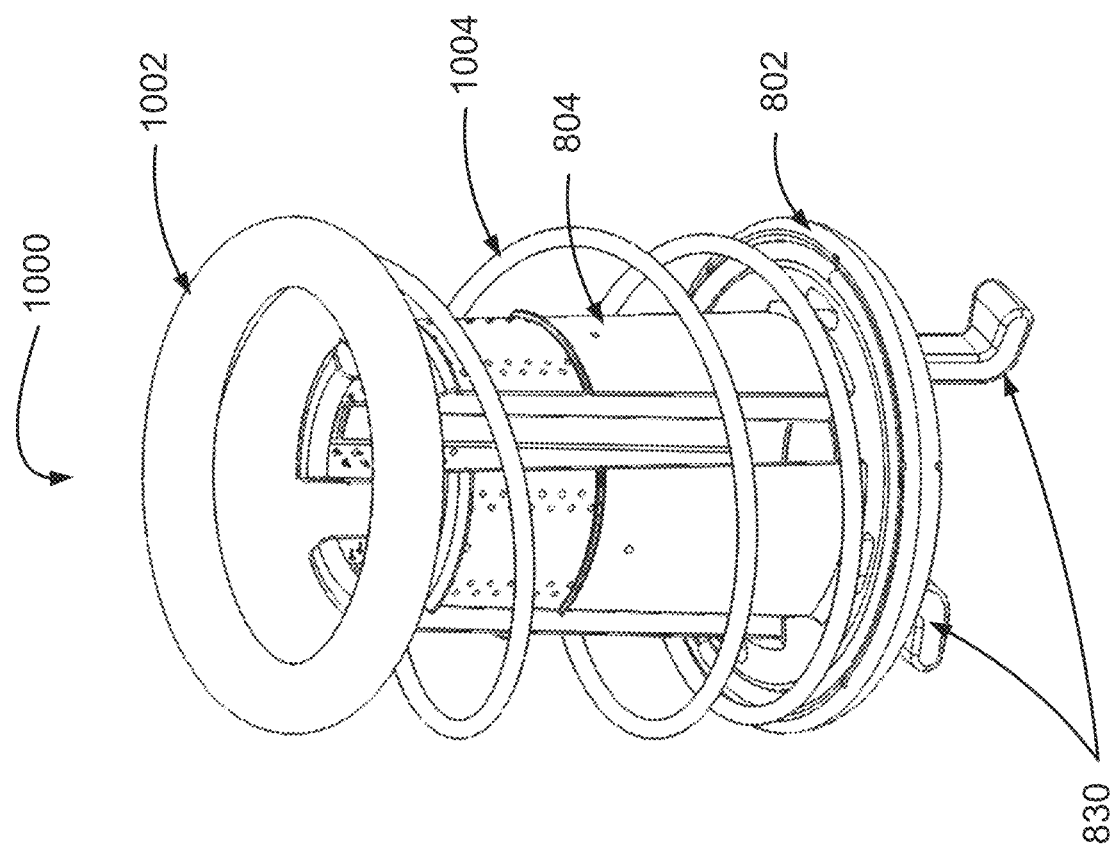
FIGURE 9A
FIGURE 9B

DELAYING PRE-TERM BIRTH

RELATED APPLICATIONS

This application is a continuation of U.S. patent application Ser. No. 15/302,190, filed on Oct. 6, 2016, which is a National Phase of PCT Patent Application No. PCT/IL2015/050402 having International Filing Date of Apr. 14, 2015, which claims the benefit of priority under 35 USC § 119(e) of U.S. Provisional Patent Application No. 61/979,006 filed on Apr. 14, 2014. The contents of the above applications are all incorporated by reference as if fully set forth herein in their entirety.

FIELD AND BACKGROUND OF THE INVENTION

The present invention, in some embodiments thereof, relates to devices and methods for delaying pre-term birth or pre-term delivery and, more particularly, but not exclusively, to devices inserted into the vagina and surrounding the cervix and to related methods.

Pre-term birth is a leading cause of perinatal morbidity and mortality.

Two major etiologies of pre-term labor causing over 50% of pre-term births are uterine premature contractions (PMC) and cervical insufficiency.

Currently there are 2 different sets of solutions—

Tocolytic (anti-contraction medication) treatment for premature contractions; and cervical cerclage or Arabin pessary for cervical insufficiency.

Additional background art includes:
(1) An article by Lawn J E, Gravett M G, Nunes T M, Rubens C E, Stanton C, Group GR, titled: "Global report on preterm birth and stillbirth (1 of 7): definitions, description of the burden and opportunities to improve data", published in BMC Pregnancy Childbirth 2010; 10 Suppl 1:S1.
(2) An article by Gynecologists ACoOa, Bulletins—Obstetrics CoP. ACOG practice bulletin no. 127: Management of preterm labor. Obstet Gynecol 2012; 119:1308-17.
(3) An article by ACOG Practice Bulletin No. 142: Cerclage for the management of cervical insufficiency. Obstet Gynecol 2014; 123:372-9.

The disclosures of all references mentioned above and throughout the present specification, as well as the disclosures of all references mentioned in those references, are hereby incorporated herein by reference.

SUMMARY OF THE INVENTION

An aspect of some embodiments of the invention relates to inserting a device into a vagina for safely supporting the cervix, preventing progression of cervical dilatation and preventing or delaying preterm labor.

An aspect of some embodiments relates to measuring forces acting upon the above-mentioned device. In some embodiments the measurements are stored in the device for subsequent retrieval. In some embodiments the measurements are relayed externally to the device, for external storage.

An aspect of some embodiments relates to making use of the force measurements. In some embodiments the use includes releasing drugs for delaying birth. In some embodiments the use includes releasing drugs for promoting birth. In some embodiments these measurements may lead to immediate release of the above mentioned device.

According to an aspect of some embodiments of the present invention there is provided a device for retarding birth including an upper ring for surrounding a cervix, an anchoring component for anchoring the device, and an elastic component for attaching the upper ring to the anchoring component, wherein the elastic component pushes the upper ring and the anchoring component apart.

According to an aspect of some embodiments of the present invention there is provided a device for retarding birth including an upper ring for surrounding a cervix, a lower ring, an anchoring component for anchoring the device, and an elastic component for attaching the upper ring to the lower ring, wherein the elastic component pushes the upper ring and the lower ring apart.

It is noted that the upper ring and the lower ring are not necessarily circular and not necessarily whole rings. The lower ring and/or the upper ring may have a non-circular shape, such as, by way of a non-limiting example, elliptical, or an asymmetric shape for surrounding the cervix. In some embodiments the lower ring and/or the upper ring may not be a closed shape, but possibly a portion of a closed shape, such as a semi-circle, semi-ellipse, or a shape corresponding to a shape which 60%, 70%, 80%, 90% or 95% closed.

According to some embodiments of the invention, further including a quick release mechanism to release the anchoring component from anchoring the device to a body of a patient.

According to some embodiments of the invention, the elastic component includes a spring.

According to some embodiments of the invention, further including a lower ring attached to the anchoring component. According to some embodiments of the invention, the anchoring component includes a lower ring attached to the elastic component.

According to some embodiments of the invention, at least one of the upper ring and the lower ring includes an elliptic shape. According to some embodiments of the invention, at least one of the upper ring and the lower ring includes a shape which is only between 60% and 95% closed.

According to some embodiments of the invention, a distance between the upper ring and the lower ring is more than a length of a cervix. According to some embodiments of the invention, a distance between the upper ring and the lower ring is less than a length of a cervix.

According to some embodiments of the invention, further including a component for releasing a drug.

According to some embodiments of the invention, further including components for measuring birth progress parameters.

According to some embodiments of the invention, further including a component for releasing a drug.

According to some embodiments of the invention, a distance between the upper ring and the lower ring is less than a length of a cervix, and the lower ring is anchored to the cervix.

According to some embodiments of the invention, a distance between the upper ring and the lower ring is more than a length of a cervix, and the lower ring is anchored to vagina walls.

According to some embodiments of the invention the lower ring is not anchored but connected to an anchoring component.

According to some embodiments of the invention, the anchoring component includes a surface arranged so as to increase friction with a surface of the cervix when the surface of the anchoring component is located against the surface of the cervix.

According to some embodiments of the invention, the anchoring component includes a plurality of projections projecting in a direction toward a surface of the cervix when the device is located surrounding the cervix. According to some embodiments of the invention, the plurality of projections point away from the upper ring.

According to some embodiments of the invention, the anchoring component is arranged to have two states: a first state in which the plurality of projections are exposed, jutting from a surface of the anchoring component, and a second state in which the plurality of projections are sheathed, concealed under a surface of the anchoring component.

According to some embodiments of the invention, the anchoring component includes depressions of at least two different depths, arranged to receive a latch having at least one projection for mating with at least one of the depressions, and wherein the anchoring component is arranged to be in the first state when the projection of the latch is located in a first depression of the anchoring component having a first depth, and to be in the second state when the projection of the latch is located in a second depression of the anchoring component having a second depth.

According to some embodiments of the invention, the latch is arranged to protrude from the anchoring component so as to be manipulated and switch the anchoring component from the first state to the second state.

According to some embodiments of the invention, the anchoring component includes a tube cut in lengthwise slits arranged so that walls of the tube flex in and out relative to a diameter of the tube.

According to some embodiments of the invention, further including a gauge attached to the elastic component and including a marking arranged to indicate a degree to which the elastic component is compressed.

According to some embodiments of the invention, further including a gauge attached to the elastic component and arranged to jut from the anchoring component according to a degree to which the elastic component is compressed.

According to some embodiments of the invention, further including a gauge attached to the elastic component and arranged to jut from the lower ring according to a degree to which the elastic component is compressed.

According to some embodiments of the invention, the elastic component includes a helical spring with a radius for surrounding the cervix.

According to some embodiments of the invention, the elastic component includes an elastic ring. According to some embodiments of the invention, the elastic ring includes an inflatable elastic ring. According to some embodiments of the invention, the elastic component includes a plurality of elastic rings. According to some embodiments of the invention, at least one of the plurality of elastic rings includes an inflatable elastic ring.

According to some embodiments of the invention, the elastic component includes a strut attached to the upper ring and to the lower ring.

According to some embodiments of the invention, the elastic component includes a plurality of struts attached to the upper ring and to the lower ring.

According to some embodiments of the invention, at least one of the plurality of struts has a different spring constant than at least one other of the plurality of struts.

According to some embodiments of the invention, further including holes in the lower ring for suturing to the cervix.

According to some embodiments of the invention, further including holes in the anchoring component for suturing to the cervix.

According to some embodiments of the invention, further including a unit for measuring a parameter associated with contractions of the device, the parameter being one of a group consisting of a frequency of contractions, force of contractions, pressure of contractions, and duration of contractions.

According to some embodiments of the invention, further including a unit for storing a value of the parameter. According to some embodiments of the invention, further including a unit for transmitting a value of the parameter to a monitoring device.

According to some embodiments of the invention, further including a unit for activating automatic release of the device from the cervix.

According to some embodiments of the invention, the unit for activating automatic release of the device from the cervix is arranged to activate automatic release based, at least in part, on the parameter exceeding a known threshold.

According to an aspect of some embodiments of the present invention there is provided a device for retarding birth including a sleeve for surrounding a cervix along a large portion of a length of the cervix, and a support strip on the sleeve designed to provide more resistance to expanding the sleeve radially at a bottom of the sleeve than at a top of the sleeve.

According to some embodiments of the invention, the support strip includes a plurality of support strips.

According to some embodiments of the invention, further including holes at the bottom of the sleeve for suturing to the cervix.

According to an aspect of some embodiments of the present invention there is provided a device for retarding birth including a sleeve for surrounding a cervix along a greater portion of a length of the cervix, a support strip on the sleeve directed along an axis of the sleeve, and a ring at least partially around the sleeve, in which when a top of the sleeve is pushed to expand radially, the support strip pivots on the ring, such that an end of the support strip near the top of the sleeve moves radially outward, and an end of the support strip near the bottom of the sleeve moves radially inward.

According to some embodiments of the invention, the support strip includes a plurality of support strips.

According to some embodiments of the invention, the ring goes all the way around the sleeve. According to some embodiments of the invention, the ring includes a plurality of rings.

According to some embodiments of the invention, the sleeve includes holes penetrating through the surface of the sleeve.

According to some embodiments of the invention, further including holes at the bottom of the sleeve for suturing to the cervix.

According to an aspect of some embodiments of the present invention there is provided a first, testing device, for testing a second device for retarding birth, the testing device including a frame for attaching a first model of a cervix, and a press for pressing a second model through the first model.

According to some embodiments of the invention, the second model is one of a group including a model of an amniotic sac with a model of a baby inside, a model of an amniotic sac with a model of a baby's head inside, a model of a baby, a model of a baby's head.

According to an aspect of some embodiments of the present invention there is provided a method of inserting a device for retarding birth including providing a device for retarding birth which includes an upper ring for surrounding a cervix, an anchoring component for anchoring the device, and an elastic component for attaching the upper ring to the anchoring component, wherein the elastic component pushes the upper ring and the anchoring component apart, inserting the device into a vagina in a compressed state such that the upper ring and the anchoring component compress the elastic component, placing the compressed device such that the upper ring surrounds the cervix, and releasing the device from the compressed state such that the upper ring moves away from the anchoring component.

According to an aspect of some embodiments of the present invention there is provided a method of inserting a device for retarding birth including providing a device for retarding birth which includes an upper ring for surrounding a cervix, a lower ring, and an elastic component for attaching the upper ring to the lower ring, wherein the elastic component pushes the upper ring and the lower ring apart, inserting the device into a vagina in a compressed state such that the upper ring and the lower ring compress the elastic component, placing the lower ring such that the lower ring surrounds the cervix, and releasing the device from the compressed state such that the upper ring moves away from the lower ring.

In some embodiments, it is an anchoring component which is between the upper ring and the lower ring which is placed, and the device is released from the compressed state such that the upper ring moves toward the fornix.

According to some embodiments of the invention, following the inserting the device into a vagina in a compressed state the upper ring is placed at its target position, and releasing the device from the compressed state such that the anchoring component moves away from the upper ring.

According to some embodiments of the invention, the anchoring component includes a lower ring attached to the elastic component, and the elastic component pushes the upper ring and the lower ring apart.

According to some embodiments of the invention, further including anchoring the anchoring component of the device against the cervix.

According to some embodiments of the invention, the anchoring component includes switching the anchoring component from a state in which anchoring projections are concealed from a surface of the cervix to a state in which the anchoring projections are exposed against the surface of the cervix.

According to some embodiments of the invention, further including anchoring the anchoring component against walls of the vagina. According to some embodiments of the invention, further including anchoring the upper ring against walls of the vagina. According to some embodiments of the invention, further including anchoring the lower ring against walls of the vagina.

According to some embodiments of the invention, following the inserting the device into a vagina in a compressed state the lower ring is placed at its target position, and releasing the device from the compressed state such that the upper ring moves away from the lower ring.

According to some embodiments of the invention, the device further includes a lower ring, and following the inserting the device into a vagina in a compressed state the lower ring is placed at its target position, and releasing the device from the compressed state such that the upper ring moves away from the lower ring.

According to some embodiments of the invention, the device further includes a lower ring, and the lower ring is located in the vagina, below the cervix and below the anchoring component.

According to some embodiments of the invention, the device further includes a lower ring, and further including using a gauge attached to the elastic component and arranged to jut from the lower ring according to a degree in which the elastic component is compressed in order to estimate a force exerted on the upper ring.

According to some embodiments of the invention, further including suturing the anchoring component to the cervix. According to some embodiments of the invention, further including suturing the anchoring component to a wall of the vagina.

According to some embodiments of the invention, following the inserting the device into a vagina in a compressed state the upper ring is placed at its target position, and releasing the device from the compressed state such that the lower ring moves away from the upper ring.

According to some embodiments of the invention, further including suturing the lower ring to the cervix. According to some embodiments of the invention, further including suturing the lower ring to a wall of the vagina.

According to an aspect of some embodiments of the present invention there is provided a method of inserting a device for retarding birth including providing a device for retarding birth which includes an upper ring for surrounding a cervix, an anchoring component for anchoring the device, the anchoring component including an anchoring extension including projections arranged to be in one of two states: a first state in which the projections are concealed from a surface of the cervix, and a second state in which the projections are exposed to the surface of the cervix, and an elastic component for attaching the upper ring to the anchoring component, wherein the elastic component pushes the upper ring and the anchoring component apart, inserting the device into a vagina in a compressed state such that the upper ring and the anchoring component compress the elastic component, placing the compressed device such that the upper ring surrounds the cervix, and switching the anchoring component from the first state to the second state such that the projections are exposed to the surface of the cervix, thereby anchoring the device against the cervix, and releasing the device from the compressed state such that the upper ring moves away from the anchoring component.

According to an aspect of some embodiments of the present invention there is provided a method of extracting a device for retarding birth from a vagina including switching an anchoring component of the device from a state in which anchoring projections of the anchoring component are exposed against a surface of the cervix to a state in which the anchoring projections of the anchoring component are concealed from the surface of the cervix, and pulling the device out of the vagina.

According to an aspect of some embodiments of the present invention there is provided a method of extracting a device for retarding birth from a vagina including activating a quick release mechanism to release an anchoring component from anchoring the device to a body of a patient, and pulling the device out of the vagina.

According to an aspect of some embodiments of the present invention there is provided a device for retarding birth including an upper ring for surrounding a cervix, an anchoring component for anchoring the device, and an elastic component for attaching the upper ring to the anchoring component, wherein the elastic component pushes the upper ring and the anchoring component apart.

According to some embodiments of the invention, further including a gauge attached to the elastic component and including physical markings arranged to indicate a degree to which the elastic component is compressed.

According to an aspect of some embodiments of the present invention there is provided a device for retarding birth including an upper ring for surrounding a cervix, an anchoring component for anchoring the device by friction with a patient's body surface.

According to some embodiments of the invention, the friction with the patient's body surface includes friction between an internal surface surrounding the cervix and the surface of the cervix.

According to an aspect of some embodiments of the present invention there is provided a method of estimating a force exerted by a uttering contraction including providing a device for retarding birth which includes an upper ring for surrounding a cervix, a lower ring, an elastic component attached to the upper ring and to the lower ring, and a gauge arranged to indicate a force exerted upon the elastic component, inserting the device into a vagina, placing the device such that the upper ring surrounds the cervix, using the gauge to estimate a force exerted on the upper ring.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings and images. With specific reference now to the drawings and images in detail, it is stressed that the particulars shown are by way of example and for purposes of illustrative discussion of embodiments of the invention. In this regard, the description taken with the drawings and images makes apparent to those skilled in the art how embodiments of the invention may be practiced.

In the drawings:

FIGS. 1A-1B are simplified illustrations of a process of birth;

FIGS. 9A and 9B are simplified illustrations of a device using the anchoring component of FIGS. 8A-8E;

DESCRIPTION OF SPECIFIC EMBODIMENTS OF THE INVENTION

Figure 2A:
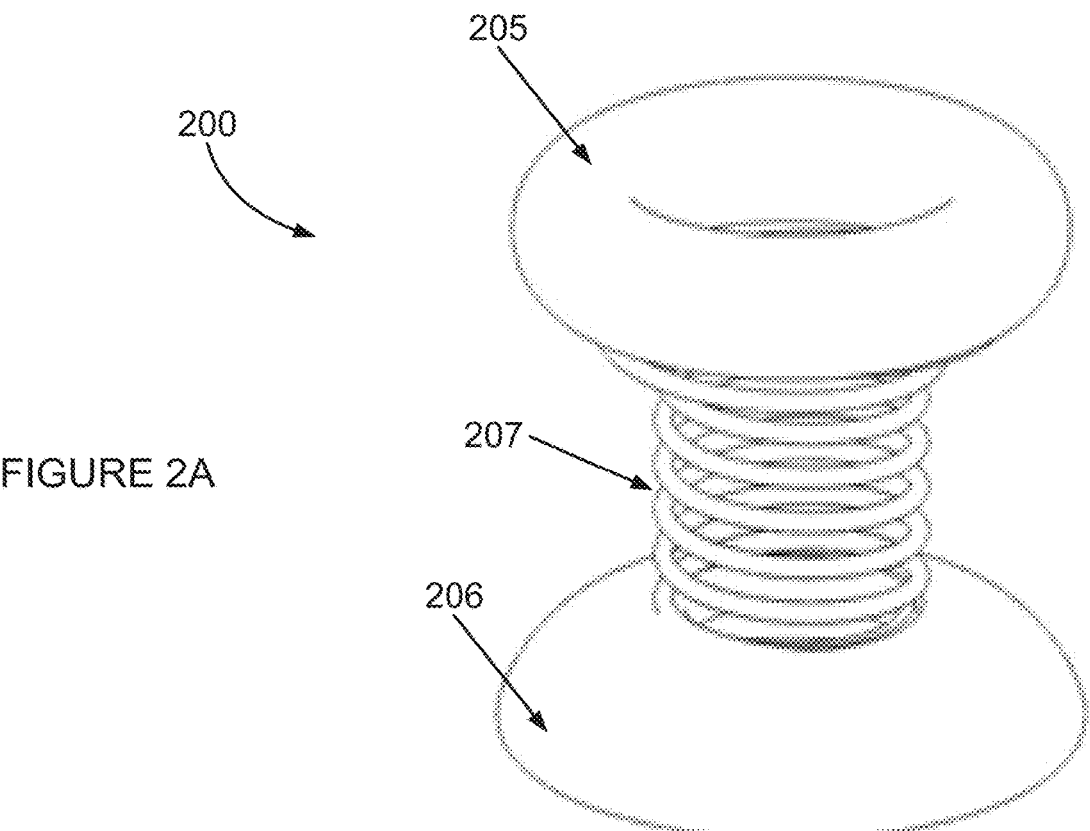
FIG. 2A is a simplified illustration of a device for retarding birth according to an example embodiment of the invention.

The present invention, in some embodiments thereof, relates to devices and methods for delaying pre-term birth or pre-term delivery and, more particularly, but not exclusively, to devices inserted into the vagina and surrounding the cervix and to related methods.

An aspect of some embodiments of the invention includes providing a device which includes an upper ring and a lower ring and an elastic mechanism such as a spring and/or elastic struts, and/or one or more dampers connecting the upper ring and the lower ring.

The terms "up" and "upper" in all their grammatical forms are used throughout the present specification and claims to describe a direction towards the uterus.

The terms "down" and "lower" in all their grammatical forms are used throughout the present specification and claims to describe a direction away from the uterus, toward the vagina and the exit of the vagina.

When the above directions are applied to a device which is outside of the body, the directions "up" and "down" apply to directions of the device as if it is inserted into a body.

In some embodiments the device is inserted into a vagina so that the upper ring surrounds the cervix in proximity to the cervical internal os.

In some embodiments the device is inserted into a vagina so that the upper ring surrounds the cervix and is pushed up high into the fornix. In some embodiments, the pushing is optionally performed by the upper ring being pushed away from the lower ring.

In some embodiments a method of inserting the device optionally includes surrounding the cervix by the upper ring, then pushing on the lower ring to push the upper ring further toward the fornix.

An aspect of some embodiments of the invention includes a gauge which potentially provides a physician an indication of a force between the upper ring and the lower ring. The gauge may optionally be felt by a physician within the vagina to assess the force, and optionally result in a measurable indication of force applied on the fornix.

In some embodiments checking the gauge is optionally performed upon installation of the device, and in some embodiments upon optionally performing check-ups.

In some embodiments a method of inserting the device optionally includes inserting the device with the elastic mechanism between the upper ring and the lower ring compressed, surrounding the cervix by the upper ring, then releasing the compression between the upper ring and the lower ring, optionally pushing the upper ring further toward the fornix in proximity to the cervical internal os or the lower ring down toward the cervical external os.

In some embodiments the lower ring is anchored to the vaginal wall.

In some embodiments the lower ring is anchored to the cervix.

In various embodiments, the elastic mechanism connecting the upper ring and the lower ring exerts a progressive; a linear; a degressive; or a constant force upon compression.

An aspect of some embodiments of the invention includes providing a device which includes a sleeve for surrounding the cervix.

In some embodiments the sleeve provides a closing force upon the proximal cervix when the uterus contracts.

In some embodiments, by limiting cervical dilatation, the biological cascade which leads to a common pathway of parturition characterized by uterine contractility, cervical ripening and fetal membrane activation is slowed or even prevented.

In some embodiments the sleeve includes support ridges designed to provide a progressive; a linear; a degressive; or a constant force for closing the proximal cervix when the uterus contracts.

An aspect of some embodiments of the invention includes providing a device which includes a sleeve surrounding the cervix and a ring surrounding the sleeve.

In some embodiments when the uterus contracts, pushing the amniotic sac in which the fetus is situated in direction of the cervix, the ring redirects a force produced, to exert a closing force upon the internal os of the cervix.

In some embodiments, by applying the closing force on the cervix in response to the contractions, the biological cascade that leads to a common pathway of parturition characterized by uterine contractility, cervical ripening and fetal membrane activation is slowed or even prevented.

In some embodiments the ring is designed to provide a progressive; a linear; a degressive; or a constant force for closing the internal os of the cervix when the uterus contracts.

An aspect of some embodiments of the invention includes providing a device which includes indications of various physiological parameters regarding uterine and/or cervical contractions.

In some embodiments the device is placed to measure contractions and provide readout of parameters relevant to the contractions. The parameters include, by way of some non-limiting examples, frequency of contractions, force of contractions, and duration of contractions. In some embodiments the parameters are optionally stored within the device. In some embodiments the parameters are optionally relayed outside the device, whether wirelessly by methods known in the art or by wire in case a patient is in position to connect to a monitoring system. The elastic component of the device is compressed and decompressed during contractions resulting in a change of length, diameter and inclination, potentially enabling readout of the above-mentioned changes.

An aspect of some embodiments of the invention includes providing a device which includes automatically releasing the anchoring to the cervix or to the vaginal wall.

In some embodiments the automatic release is optionally based on a feedback process based on force and/or frequency of uterine contractions, optionally when above a known threshold.

An aspect of some embodiments of the invention includes providing a device which includes drug eluting which is optionally based on demand, optionally based on indications of various physiological parameters regarding uterine contractions and/or cervical dilation and/or effacement and/or the state of the fetus and/or the gestational age and/or other obstetrical consideration and/or any of the measurement parameters described herein.

In some embodiments of the invention, the two etiologies mentioned above as causing more than 50% of pre-term births, PMC and cervical insufficiency, are both treated, thereby potentially obviating a need for providing different treatment for the different etiologies, and also potentially enabling a treatment which is useful in treating both of the etiologies and others.

An aspect of some embodiments of the invention includes providing an anchoring extension for the device, where the anchoring extension is arranged to increase friction between the anchoring extension and a surface of the patient's body.

In some embodiments the anchoring extension may be a tube-like shape for surrounding the cervix, including many sharp, or pin-like, or bristle-like protrusions for increasing friction between the anchoring extension and a surface of a cervix against which the anchoring extension is placed.

In some embodiments the anchoring extension may be a tube-like shape for surrounding the cervix, including many protrusions about an inside of the tube, for increasing friction between the anchoring extension and a surface of a cervix against which the anchoring extension is placed.

In some embodiments the anchoring extension may include protrusions such as described above, optionally deployed on an outside circumference of a lower ring, for increasing friction between the lower ring and a surface of a vagina against which the lower ring is placed.

Some potential benefits of using anchoring extensions include:

In some embodiments, no suture is required, and the device is easily and simply deployed, potentially without anesthesia, and potentially in an out-patient or clinic procedure.

In some embodiments, suturing is optionally used, but less suturing may be required, potentially resulting in a simpler procedure, potentially resulting in less damage to the sutured organ, and potentially resulting in better device retention.

An aspect of some embodiments of the invention includes providing a gauge for estimating by how much the device contracts and/or expands.

In some embodiments, the gauge potentially enables a physician to feel by how much the gauge protrudes from a lower ring of the device, potentially even with a gloved hand.

In some embodiments, by estimating by how much the gauge protrudes from the lower ring the physician may estimate a change in length of the device, thereby potentially estimating force or pressure on the device.

In some embodiments, by estimating force or pressure on the device, the physician may tell if the device exerts a desired pressure on the fornix.

In some embodiments, by estimating force or pressure on the device, the physician may tell pressure of a contraction of the uterus.

In some embodiments of the invention a setup for testing the device is also optionally provided. The testing setup optionally includes a model of a cervix, optionally constructed of a flexible membrane which mimics a behavior and shape of a cervix and walls of a vagina. In some embodiments the cervix model also mimics a bottom of a uterus where it is connected to the cervix.

In some embodiments the testing setup includes a press for optionally grasping and pushing a model of an amniotic sac with a model baby, or at least a model baby's head inside it, against the model of the cervix.

In some embodiments the testing setup enables to optionally measure forces and or stresses applied by a specific sized amniotic sac with a baby model against a specific sized cervix model, and optionally to measure forces and or stresses applied by a specific sized amniotic sac with a baby model and a specific sized cervix model against a specific sized device for preventing pre-term birth.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Before explaining at least one embodiment of the invention in detail, it is to be understood that the invention is not necessarily limited in its application to the details set forth in the following description. The invention is capable of other embodiments or of being practiced or carried out in various ways.

Reference is now made to FIGS. 1A-1B, which are simplified illustrations of a process of birth.

A main function of a cervix 102 is its role in childbirth. As a fetus 104 descends in preparation for birth, a presenting part, usually the head 106, rests on and is supported by the cervix 102. The fetus 104 is surrounded by amniotic fluid 105. This stage is depicted by FIG. 1A.

This support begins to give way as the cervix 102 starts to dilate when the uterus 103 begins its contractions. This stage is depicted by FIG. 1B.

During childbirth, the cervix 102 must dilate to a diameter greater than the fetal head 106—the exact size depends on the gestational age as it is pushed from the uterus 103 to the vagina 101.

Toward childbirth the cervix 102 also becomes shorter, known as effacement.

Reference is now made to FIG. 2A, which is a simplified illustration of a device for retarding birth according to an example embodiment of the invention.

FIG. 2A depicts an upper ring 205 and a lower ring 206 connected to each other by an elastic component 207.

Figure 2B:
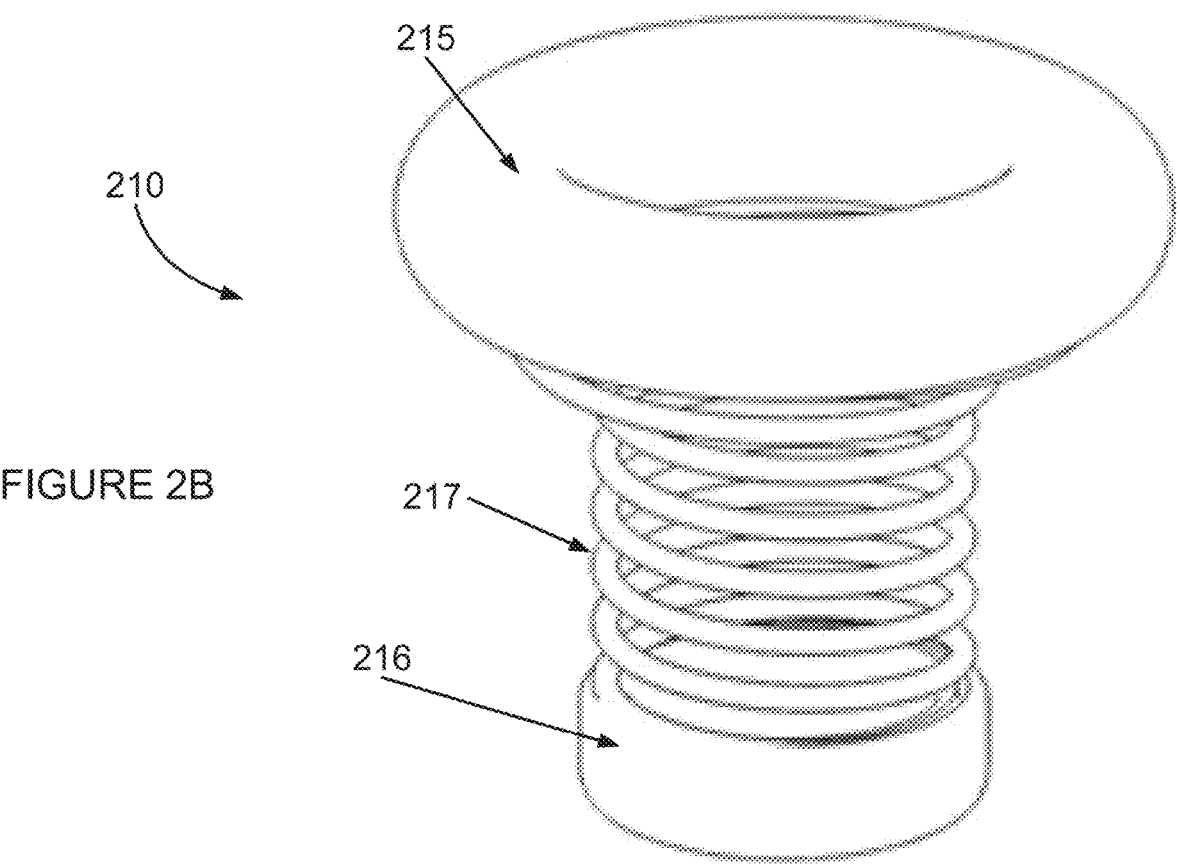
FIG. 2B is a simplified illustration of a device for retarding birth according to another example embodiment of the invention.
Figure 2C:
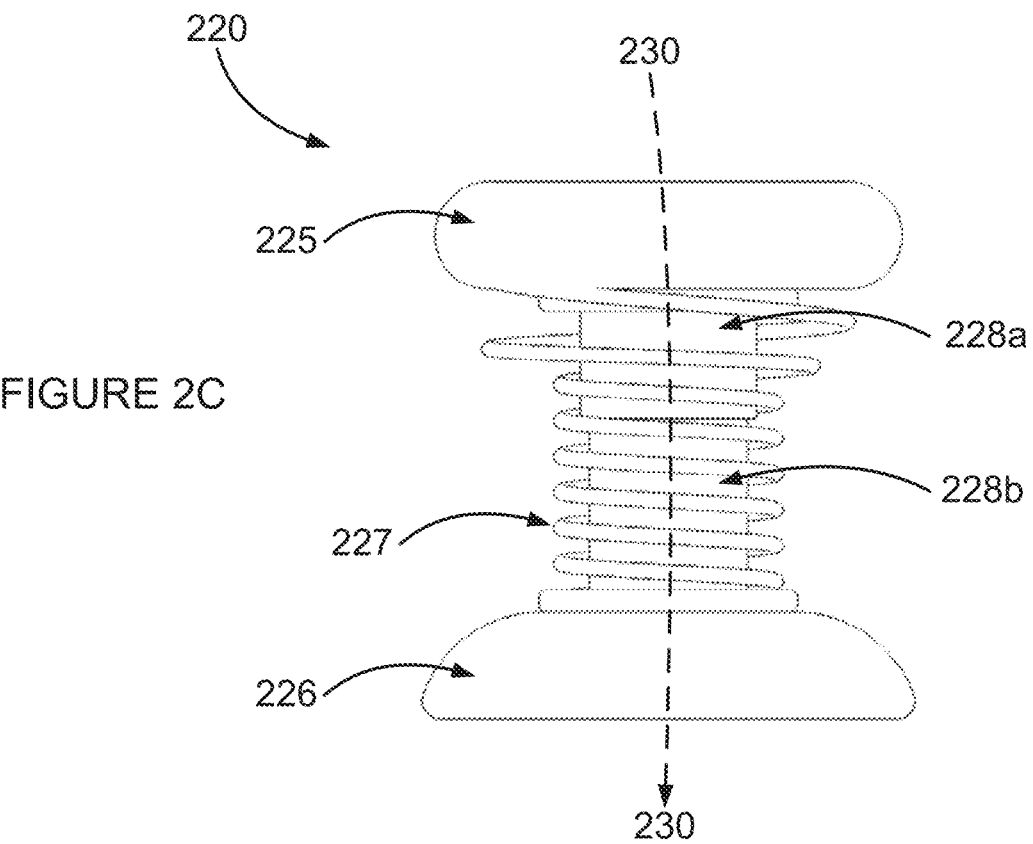
FIGS. 2C and 2D are simplified illustrations of a device for retarding birth according to yet another example embodiment of the invention.
Figure 2D:
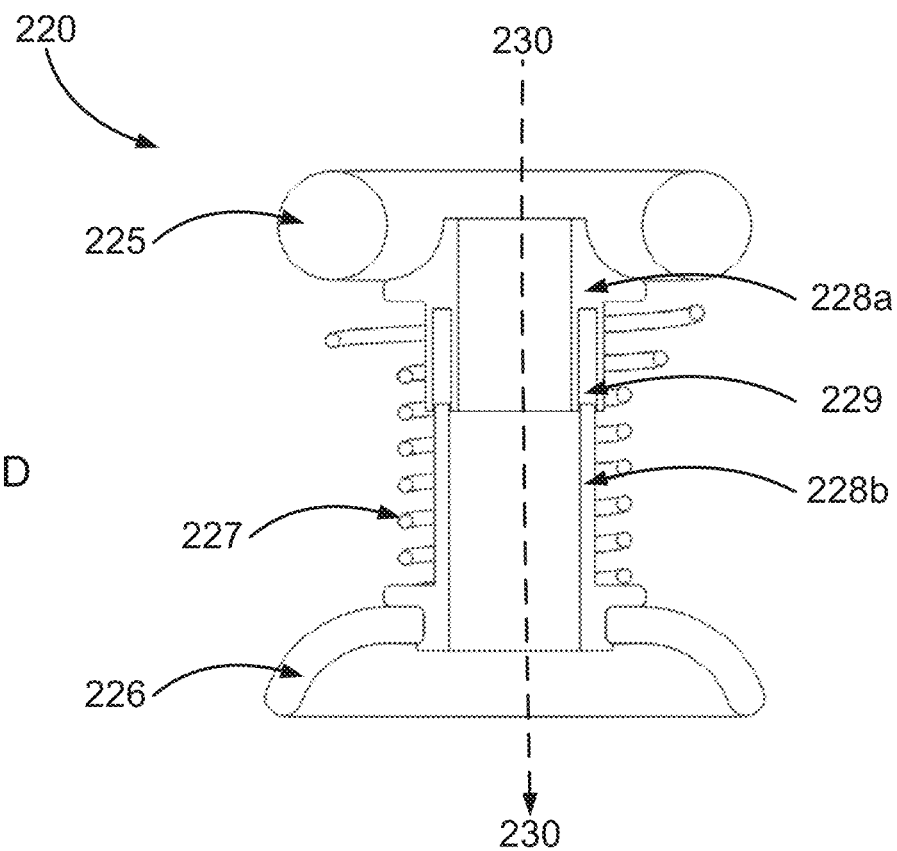

The example embodiment depicted in FIG. 2A depicts the elastic component 207 as a helical spring attached to the upper ring 205 and to the lower ring 206 In some embodiments the elastic component may include one or more elastic struts, or dampers (not shown in FIG. 2A, an example embodiments is shown in FIGS. 2C and 2D).

In some embodiments the upper ring 205 is rounded so as to optionally provide a rounded edge to the upper ring pushing on the fornix wall surrounding the cervix in proximity to the internal os.

In some embodiments the lower ring 206 extends radially wider than the elastic component 207, so as to reach a wall of the vagina and anchor against the wall of the vagina.

In some embodiments the lower ring 206 is an anchoring component, as depicted in FIG. 2A-2F.

In some embodiments the lower ring is not necessarily an anchoring component, and the anchoring component may optionally include some other mechanism for anchoring the device to the cervix, and/or for anchoring the device to the vagina walls.

In some embodiments the elastic component 207 is attached to a lower ring 206 which, as described above, is not the anchoring component.

In some embodiments the lower ring 206 includes holes (not shown) for suturing to the wall of the cervix.

In some embodiments the shape of the device 200 is not necessarily cylindrical, but may be a skewed cylinder, or a conical shape, or a skewed conical shape. In some embodiments a skewed shape is achieved by having a different thickness of the spring coils on one side than another or different diameters of the spring coils on one side than another.

In some embodiments ventilation holes are included in the lower ring 206 and/or in the upper ring 205, potentially enabling fluid discharge.

Reference is now made to FIG. 2B, which is a simplified illustration of a device for retarding birth according to another example embodiment of the invention.

FIG. 2B depicts an upper ring 215 and a lower ring 216 connected to each other by an elastic component 217.

In some embodiments the lower ring 216 is approximately the same radius as the elastic component 217, so as to anchor near the bottom of the cervix.

In some embodiments the lower ring 216 includes holes (not shown) for suturing to the cervix.

In some embodiments ventilation holes are included in the lower ring 216 and/or in the upper ring 215, potentially enabling fluid discharge.

Reference is now made to FIGS. 2C and 2D, which are simplified illustrations of a device 220 for retarding birth according to yet another example embodiment of the invention.

FIG. 2C depicts a side view and FIG. 2D depicts a side cross-sectional view of the device 220.

The device 220 includes an upper ring 225 and a lower ring 226 connected to each other by an elastic strut 228a 228b.

In some embodiments, as depicted in FIGS. 2C and 2D the elastic strut 228a 228b is included as well as a spring 227.

In some embodiments (not shown) the device 220 includes a strut 228a 228b and no spring 227.

The side cross-sectional view 2D of the device 220 depicts an example embodiment of a portion 228b of the strut being designed to enter within a space in another portion 228a of the strut.

Figure 2E:
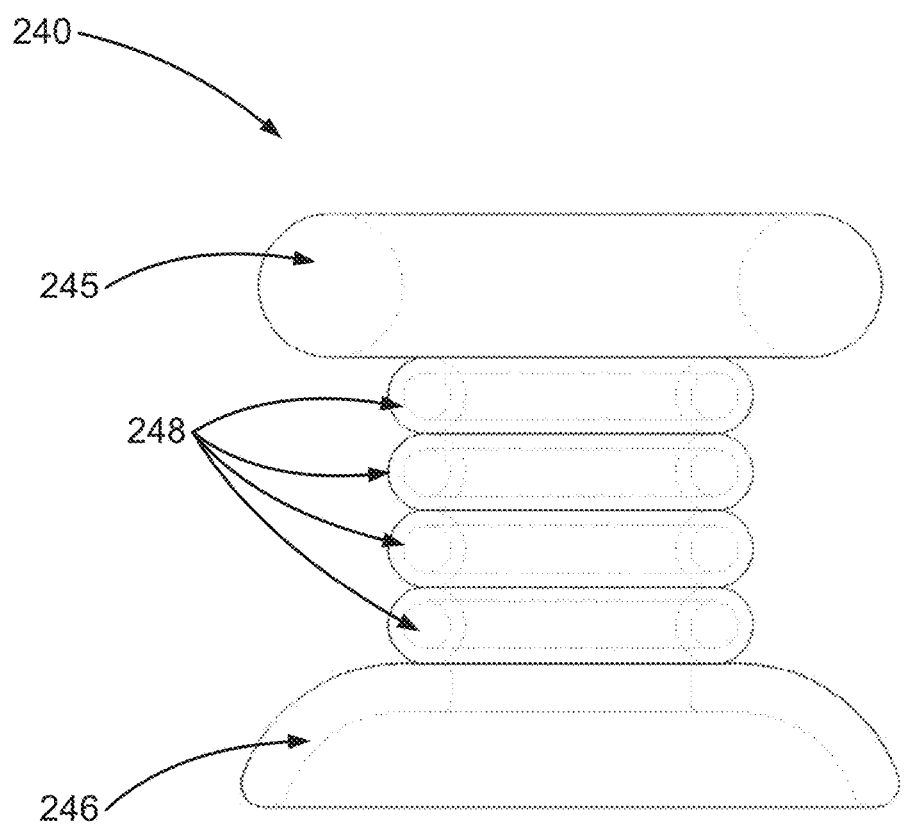
FIGS. 2E and 2F are simplified illustrations of a device for retarding birth according to yet another example embodiment of the invention.
Figure 2F:
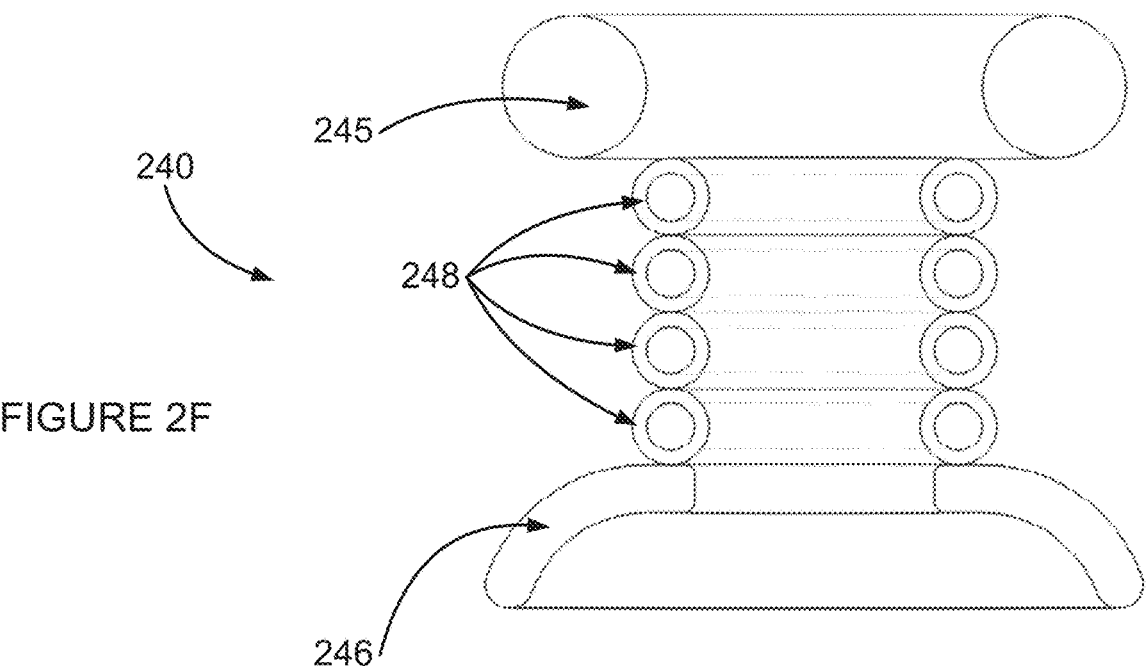

Reference is now made to FIGS. 2E and 2F, which are simplified illustrations of a device 240 for retarding birth according to yet another example embodiment of the invention.

FIG. 2E depicts a side view and FIG. 2F depicts a side cross-sectional view of the device 240.

The device 240 includes an upper ring 245 and a lower ring 246 connected to each other by one or more elastic torus-shaped rings 248 or tires.

The elastic component for the example embodiment of FIGS. 2E and 2F is optionally made out of a set of hollow tubes which can optionally vary in geometry, by way of a non-limiting example, a smaller diameter tube at the top, and a tube with a shape of an ellipse.

When contracted the tubes potentially collapse slowly, acting as a spring, while also having properties of an elastic sleeve—expanding in an outer diameter while activating a force in the direction of the expansion resulting in pressure on the cervix to close its dilation.

In some embodiments the number of tubes can optionally vary between 1 to 10 mm, an inner diameter of a space within a ring 248 optionally ranges from 10 to 30 mm, an external diameter of a ring 248 optionally ranges from 30 to 60 mm.

Figure 2G:
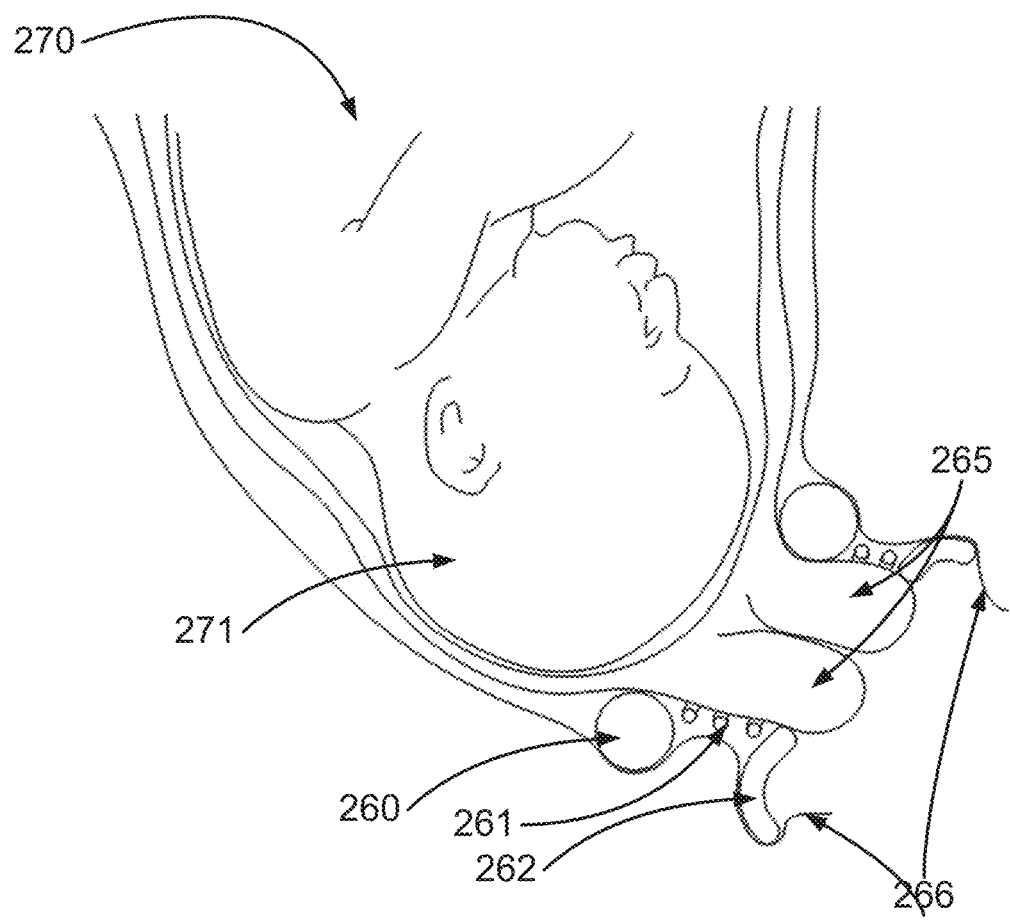
FIG. 2G is a simplified illustration of a device for retarding birth according to still another example embodiment of the invention, depicted in reference to a fetus in the uterus and the cervix.

Reference is now made to FIG. 2G, which is a simplified illustration of a device for retarding birth according to still another example embodiment of the invention, depicted in reference to a cervix.

FIG. 2G depicts a fetus 270 with its head 271 against the cervix 265, and a device for retarding birth in place according to an example embodiment of the invention.

An upper ring 260, an elastic component 261 and a lower ring 262 of the device are shown.

The example device is shown with the lower ring 262 anchored on the cervix 265.

It is noted that other embodiments (not shown in FIG. 2G) may have the lower ring 262 anchored on the vagina wall 266.

It is noted that the upper ring 260 the elastic component 261 and the lower ring 262 are not aligned as a perfect cylinder, but are rather skewed, as may often be the case in real life situations. As described elsewhere herein, for example regarding FIGS. 2E and 2F, the device may be asymmetrically shaped.

In some embodiments the anchoring component is not ring-shaped as depicted herein, but shaped asymmetrically. By way of a non-limiting example, a ring shaped anchoring component may be suitable for anchoring to the cervix, and a different shape for anchoring to the walls of the vagina.

As is known the size and width of the cervix is different in different women and different during stages of pregnancy. In some embodiment the upper ring, the elastic mechanism and the lower ring are to fit and adjust to the different situations and stages of pregnancy.

In some embodiments of the invention the shape and angle of the anchoring element is made to conform to anchoring on the walls of the vagina.

Figure 3:
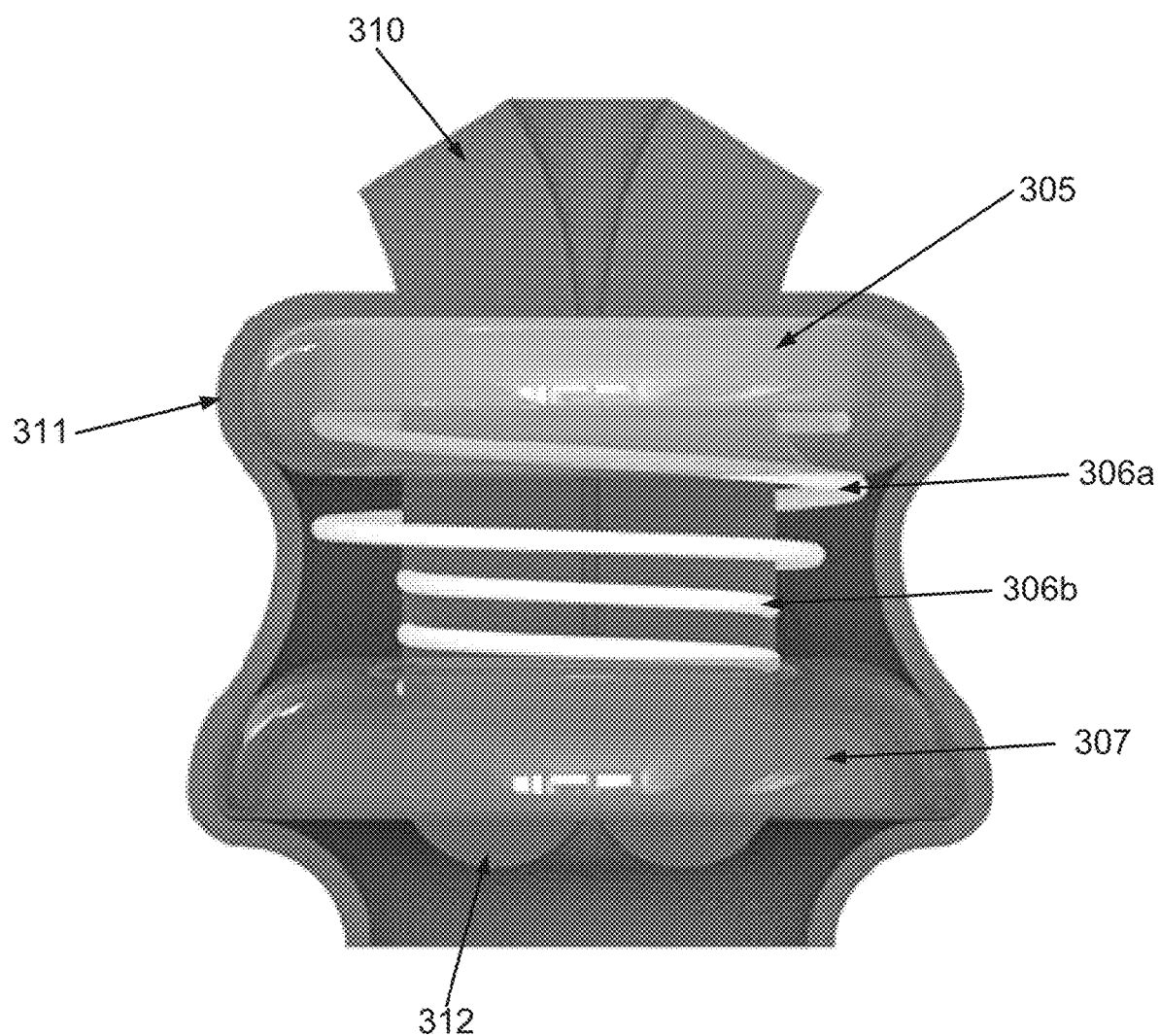
FIG. 3 is a simplified illustration of a device for retarding birth according to yet another example embodiment of the invention, depicted in reference to a cervix.

Reference is now made to FIG. 3, which is a simplified illustration of a device for retarding birth according to yet another example embodiment of the invention, depicted in reference to a cervix.

FIG. 3 depicts an upper ring 305 and a lower ring 307 connected to each other by an elastic component 306a 306b.

FIG. 3 depicts the upper ring 305 pushed up into an area termed the fornix of the vagina. The fornix of the vagina is the deepest portion of the vagina, extending into a recess created by the upper vaginal portion and the cervix.

The upper ring 305 surrounds the cervix 310, and is surrounded by walls 311 of the vagina.

FIG. 3 depicts an example embodiment where the external os 312 of the cervix 310 protrudes from the lower ring 307.

In some embodiments the inner diameter of the upper ring 305 ranges from 20-50 mm. In some embodiments the outer diameter of the upper ring 305 ranges from 30-60 mm.

In some embodiments a distance between the upper ring 305 and the lower ring 307 ranges from 30-100 mm. such embodiments are typically embodiments for anchoring on a vaginal wall.

In some embodiments a distance between the upper ring 305 and the lower ring 307 ranges from 10-50 mm. such embodiments are typically embodiments for anchoring on a cervix.

In some embodiments the device for retarding birth includes an upper ring, a lower ring and an elastic mechanism such as a spring or a damper connecting between the upper ring and the lower ring. The elastic mechanism may optionally operate as a shock absorber to smooth out, store or dampen shock impulse, and dissipate energy applied by forces of uterine contractions.

In some embodiments the device is to be positioned inside a vagina, surrounding the cervix.

In some embodiments the lower ring is optionally anchored in place by internal body pressure applied by the vaginal wall and pelvic bones against the lower ring.

In some embodiments the lower ring is optionally anchored in place by an anchoring component exerting friction onto the cervix.

In some embodiments the device is anchored in place without resort to suturing the device to a patient's body.

In some embodiments additional support is optionally achieved by suturing the lower ring to the distal, bottom part of the cervix.

In some embodiments installation of the device is optionally achieved by inserting the device while the elastic component is in a compressed mode (top ring and lower ring are closer to one another), placing the lower ring at its target position and gradually releasing the compression lock to allow the top ring to elevate towards the fornix. Releasing the lock optionally provides control over a final length of the elastic component and its orientation, optionally to fit the curvature of the cervix.

In some embodiments installation of the device is optionally achieved by inserting the device while the elastic component is in a compressed mode (top ring and lower ring are closer to one another), placing the top ring at its target position and gradually releasing the compression lock to allow the lower ring to lengthen along the cervix. Releasing the lock optionally provides control over a final length of the elastic component and its orientation, optionally to fit the curvature of the cervix.

In some embodiments the top ring acts as a cuff holding on to a cross section of a proximal, top, part of the cervix in proximity to the internal os. During contraction, the device potentially enables a vector change of the applied force and the applied pressure, potentially redirecting energy to be dispersed on a larger surface of device or the cervix, potentially enabling cervix tissue to better resist stress, dilatation and shortening or effacement. Releasing the pressure potentially minimizes the risk of ischemia atrophy or rupture of the cervix or uterus.

In some embodiments a portion of contraction energy is transferred through the anchoring component and/or lower ring to the vaginal wall and/or the pelvic bones and/or stitches suturing and anchoring the device. Potentially, when contraction comes to an end, the device pushes the top ring back into the fornix, optionally again providing circumferential support high on the cervix in proximity to the internal os.

In some embodiments the elastic component, whether spring, piston, or other, is produced in different lengths, diameters and orientation. Optionally the elastic component is pre-set to a specific orientation, not necessarily keeping the upper ring and lower ring parallel. Some example methods include: using a shape memory spring, which aspires to return to its original state; pre-shaping a spring by adjusting its coils in relation to one another by manufacturing or by attachments to the coils to pull and distance one from the other.

In some embodiments shaping the device potentially achieves a better anchoring to a vaginal wall and/or more control over a distribution of stress over the device while contracted.

It is noted that the cervix changes its orientation angle over duration of pregnancy, so being able to adjust an inserted device to changing geometry potentially provides an advantage, potentially fitting a variance of differently shaped cervixes and/or fitting a change of anatomy dimensions throughout a pregnancy.

In some embodiments the rings are optionally made of a low hardness material to enable the rings to adapt to the female anatomy.

In some embodiments, the rings are inflated, optionally in place, potentially achieving good anchorage of the lower ring to the vaginal wall and/or to the cervix and/or a high and tight hold of the upper ring near the top of the cervix in proximity to the internal os.

In some embodiments the rings are produced in a variety of annular geometric shapes and sizes to match a diversity of sizes and shapes of a cervix, and provide individual, modular solutions per need.

In some embodiments the device achieves inclination of the cervix.

It is noted that the device for retarding birth is optionally indicated for either one or both of premature contractions and cervical insufficiency and optionally other indications such as an over distended uterus, twins and multi gestational pregnancies.

In some embodiments, a version indicated for cervical insufficiency is optionally sutured to the cervix.

In some embodiments, a version indicated for cervical insufficiency is optionally sutured to the cervix in a position lower than a classic McDonald or Shirodkar cerclage are sutured.

In some embodiments, a version indicated for premature contractions is anchored to the vaginal wall.

A Bolstered Sleeve Embodiment

Figure 4A:
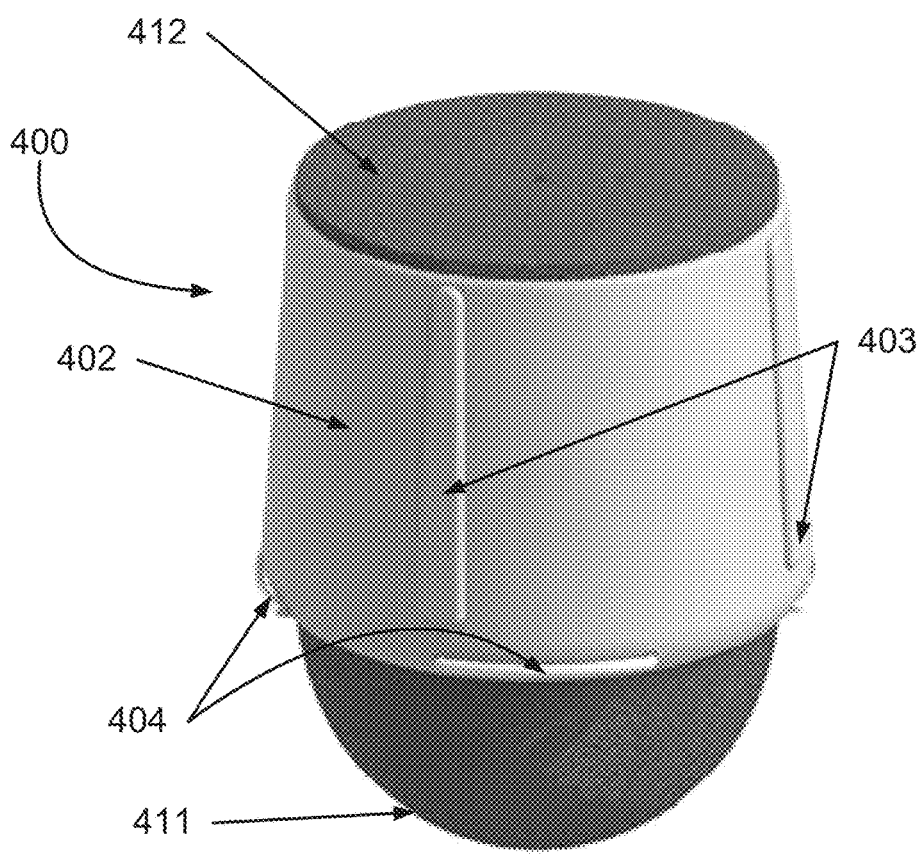
FIG. 4A is a simplified illustration of a device for retarding birth according to still another example embodiment of the invention, also depicted in reference to a cervix.

Reference is now made to FIG. 4A, which is a simplified illustration of a device 400 for retarding birth according to still another example embodiment of the invention, also depicted in reference to a cervix.

FIG. 4A depicts a sleeve 402 for surrounding a cervix 412.

In some embodiments, the sleeve 402 surrounds a large portion of the length of the cervix 412, so as to disperse stress.

FIG. 4A also depicts the external os 411 of the cervix 412 emerging from the sleeve 402.

In some embodiments the device 400 optionally includes one or more support strips 403 on or in the sleeve 402.

In the embodiment depicted in FIG. 4A the support strips 403 are oriented along a length of the sleeve 402.

In some embodiments the support strip(s) may be oriented differently, such as, by way of a non-limiting example, in a helical direction around the sleeve (not shown) or in a circumferential direction around the sleeve (not shown).

In the embodiment depicted in FIG. 4A the support strips 403 are constructed so as to have a varying thickness along a length of the sleeve 402.

In some embodiments the support strips 403 are optionally designed to provide more resistance to expanding the sleeve 402 radially at a bottom of the sleeve 402 than at a top of the sleeve 402.

In some embodiments the support strips 403 are optionally designed to provide more resistance to expanding the sleeve 402 radially at a top of the sleeve 402 than at a bottom of the sleeve 402.

In some embodiments of the invention the sleeve 402 optionally includes holes at a bottom of the sleeve 402 for optionally suturing 404 the sleeve 402 to the lower part 411 of the cervix 412.

In some embodiments, the sleeve 402 is optionally made of a material such as, by way of a non-limiting example, synthetic polymers such as silicone, rubber, or neoprene.

In some embodiments, the sleeve 402 and the support strips 403 are made in one piece of the same material.

In some embodiments, the support strips 403 are made separately and attached to and/or inserted into the sleeve 402. In some embodiments one or all of the support strips are made of a different material than the sleeve 402, optionally of a material which supports tuning the stiffness of the device 400.

In some embodiments the separate support strip(s) 403 are attached to a standard attachment in the sleeve 402.

In some embodiments ventilation holes are included in the sleeve 402, potentially enabling fluid discharge.

Figure 4B:
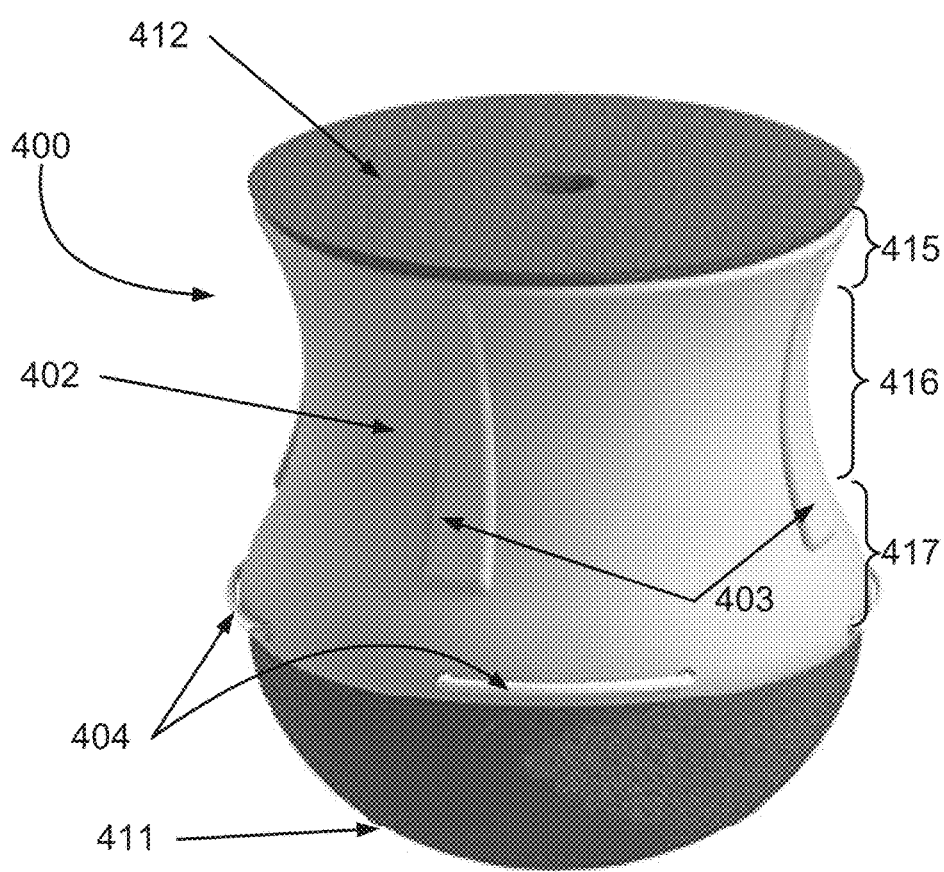
FIG. 4B is a simplified illustration of the example embodiment of FIG. 4A, depicted in reference to a cervix under uterine contraction.

Reference is now made to FIG. 4B, which is a simplified illustration of the example embodiment of FIG. 4A, depicted in reference to a cervix under uterine contraction.

FIG. 4B depicts the sleeve 402 giving way differentially under uterine contraction. A top portion 415 of the sleeve 402 is pushed aside, possibly due to the amniotic sac and possibly the fetus head trying to push into the cervix 412. A bottom portion 417 of the sleeve 402 is bolstered by the support strips 403 and does not expand, or expands less. Forces caused by the optionally differentially stretch resistant support strips 403 causes the sleeve to constrict in a middle portion 416 of the sleeve 402.

In some embodiments the bolstered sleeve 402 optionally has circumferential support strips 403, optionally with changing thickness, to provide resistance to strains actuated by contractions, optionally with a gradually inclining opposed force closing the cervix 412 tighter at a middle portion 416 of the sleeve 402 as contractions and pressure progresses.

In some embodiments the sleeve 402 optionally includes ventilation holes (not shown).

In some embodiments ventilation holes are included in the sleeve 402, potentially enabling fluid discharge.

In some embodiments the device 400 optionally includes bolster shapes other than shown in FIGS. 4A and 4B, or even a variety of bolster shapes on a same embodiment.

In some embodiments the device 400 optionally includes a friction enhancing surface pattern or a friction decreasing surface pattern, to achieve friction or decrease friction with the cervix 412.

In some embodiments the device 400 is optionally stitched to a distal part of the cervix 412.

A Ring Embodiment

Figure 5A:
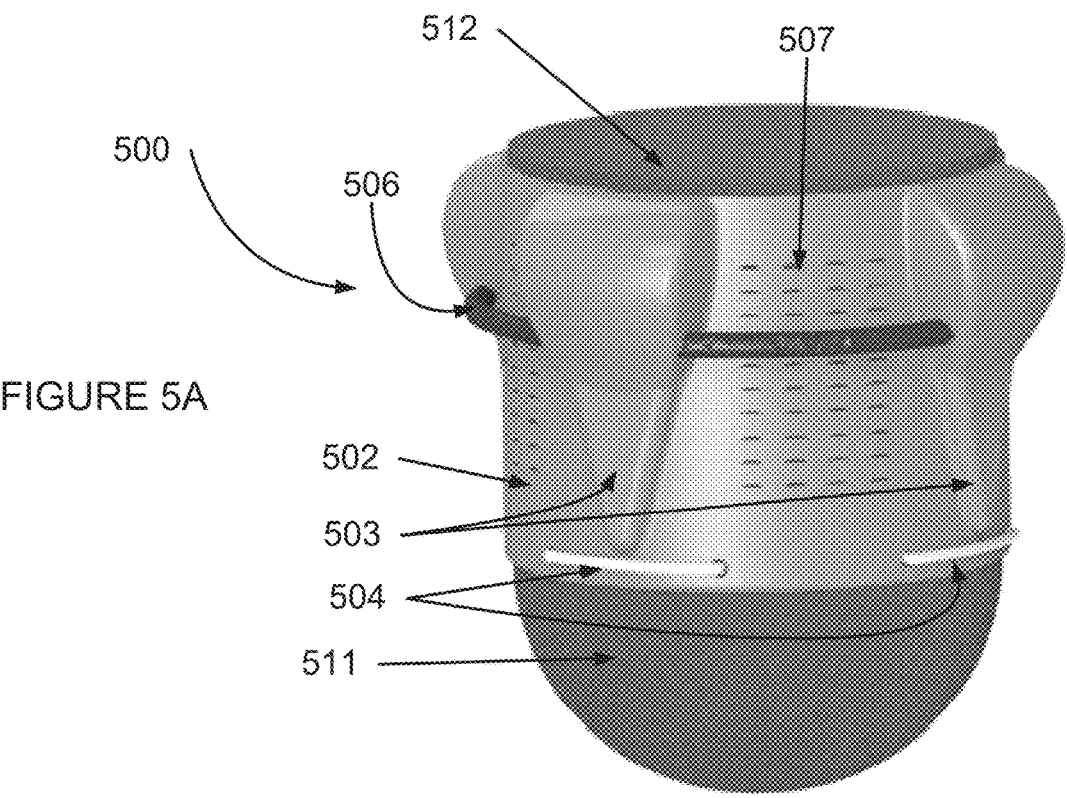
FIG. 5A is a simplified illustration of a device for retarding birth according to yet another example embodiment of the invention, also depicted in reference to a cervix.

Reference is now made to FIG. 5A, which is a simplified illustration of a device 500 for retarding birth according to yet another example embodiment of the invention, also depicted in reference to a cervix.

FIG. 5A depicts a sleeve 502 for surrounding a cervix 512.

In some embodiments, the sleeve 502 surrounds a large portion of the length of the cervix 512, so as to disperse stress.

FIG. 5A also depicts the external os 511 of the cervix 512 emerging from the sleeve 502.

In some embodiments the device 500 optionally includes one or more support strips 503 on or in the sleeve 502.

In some embodiments the device 500 optionally includes a ring 506 at least partially around the sleeve 502.

In the embodiment depicted in FIG. 5A the support strips 503 are constructed so as to have a varying thickness along a length of the sleeve 502. The varying thickness is optional, in some embodiments the thickness may be constant, and/or vary differently than depicted in FIG. 5A.

In some embodiments of the invention the sleeve 502 optionally includes holes at a bottom of the sleeve 502 for optionally suturing 504 the sleeve 502 to the bottom part of the cervix.

Figure 5B:
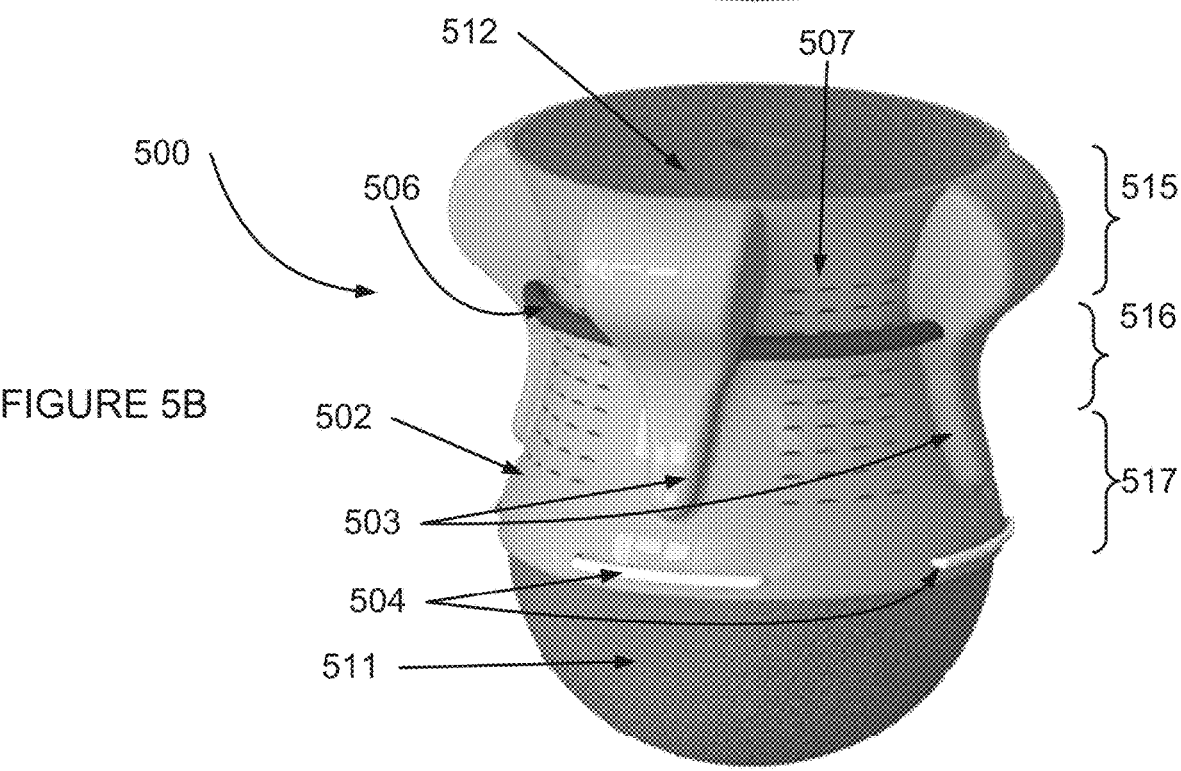
FIG. 5B is a simplified illustration of the example embodiment of FIG. 5A, depicted in reference to a cervix under uterine contraction.

Reference is now made to FIG. 5B, which is a simplified illustration of the example embodiment of FIG. 5A, depicted in reference to a cervix under uterine contraction.

FIG. 5B depicts the sleeve 502 giving way differentially under uterine contraction. A top portion 515 of the sleeve 502 is pushed to expand radially, possibly due to the amniotic sac and possibly the fetus head trying to push into the cervix 512.

In the embodiment of FIG. 5B, when the top portion 515 of the sleeve 502 is pushed to expand radially, the support strip(s) 503 pivots on the ring 506, such that an end of the support strip(s) 503 near the top of the sleeve 502 moves radially outward, and an end of the support strip(s) 503 near the bottom of the sleeve moves radially inward.

The middle portion 516 of the sleeve 502 includes the ring 506, which does not expand, or expands less. Forces caused by the uterine contraction optionally cause the sleeve 502 to pivot around the ring 506, constrict in the middle portion 516 of the sleeve 502, and optionally cause the bottom portion 517 to pivot and close the cervix 512.

In some embodiments the sleeve 502 optionally includes ventilation holes 507.

In some embodiments the ring 506 goes all the way around the sleeve 502. In some embodiments the ring 506 goes only part of the way around the sleeve 502.

In some embodiments a number of rings (506) (not shown) surround the sleeve at intervals.

In some embodiments the ring 506 is a rigid or substantially rigid ring. In some embodiments the ring 506 is an elastic ring.

In some embodiments the ring embodiment includes circumferential support bolsters with a rigid ring 506 inserted through to provide resistance to strains actuated by contractions.

In some embodiments, during contraction, the bolsters optionally change in diameter. Such embodiments optionally resulting in a clamping of the ring 506, potentially using strains and deformation of the cervix 512 to tighten around the cervix 512.

In some embodiments opposing forces are used to stop progression of birth.

In some embodiments the device 500 optionally includes bolster shapes other than shown in FIGS. 5A and 5B, or even a variety of bolster shapes on a same embodiment.

In some embodiments the device 500 optionally includes a friction enhancing surface pattern or a friction decreasing surface pattern, to achieve friction or decrease friction with the cervix 512.

In some embodiments the device 500 is optionally stitched to a distal part of the cervix.

An Embodiment Including Measurement of Birth Progress Parameters

In some embodiments of the invention the birth retardation device is optionally used as a mechanism to measure birth progress parameters, such as, by way of a non-limiting example, contraction pressure and contraction frequency.

Figure 5C:
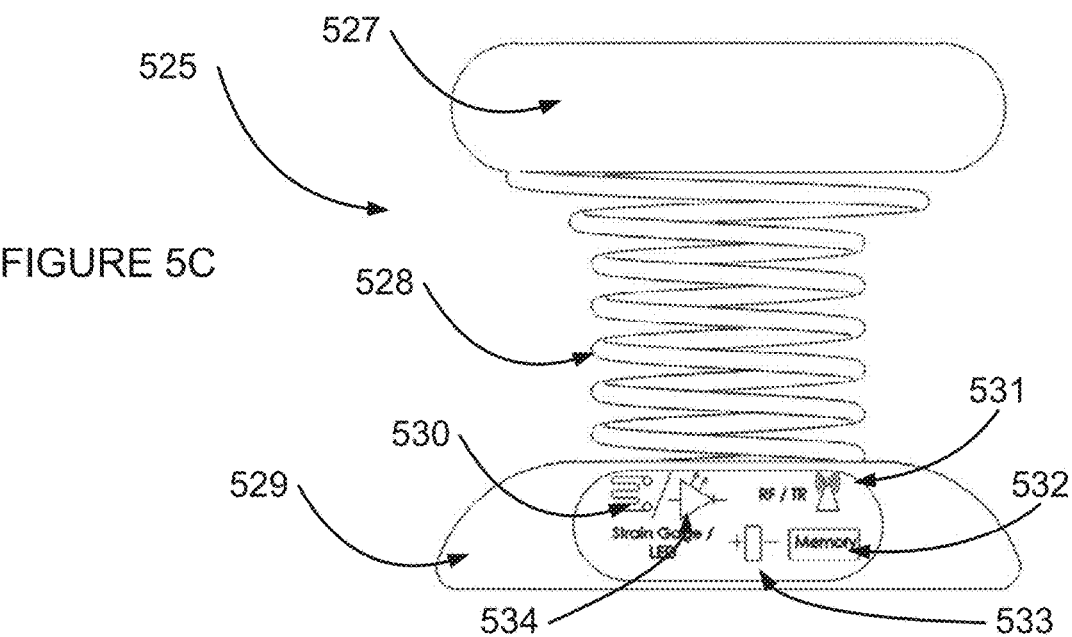
FIG. 5C is a simplified illustration of a device for retarding birth according to still another example embodiment of the invention.

Reference is now made to FIG. 5C, which is a simplified illustration of a device 525 for retarding birth according to still another example embodiment of the invention.

FIG. 5C depicts the device 525, the upper ring 527, the elastic component 528 and the lower ring 529.

In example embodiments depicted by FIG. 5C, the device 525 includes electrical components for measuring at least some of the above-mentioned birth progress parameters.

In some embodiments the device 525 optionally includes a Printed Circuit Board with at least some of the electrical components connected thereto.

In some embodiments the device 525 optionally includes a battery 533.

In some embodiments the device 525 optionally includes an RF communication device 531.

In some embodiments the device 525 optionally includes a contraction sensing component 530, such as, by way of a non-limiting example, a strain gauge. In some embodiments the device 525 optionally includes a signal amplifier 534 for amplifying signals from the contraction sensing component 530.

In some embodiments the device optionally transmits a contraction signal via RF to an external receiver (not shown).

In some embodiments the RF communication device 531 comprises a Bluetooth transmitter, and optionally transmits a contraction signal to an external Bluetooth receiver (not shown). In some embodiments the external Bluetooth receiver (not shown) may be included in a device such as smartphone for real time contraction monitoring by the doctor and/or the patient.

In some embodiments the device 525 optionally includes memory 532 for storing measurements.

Figure 5D:
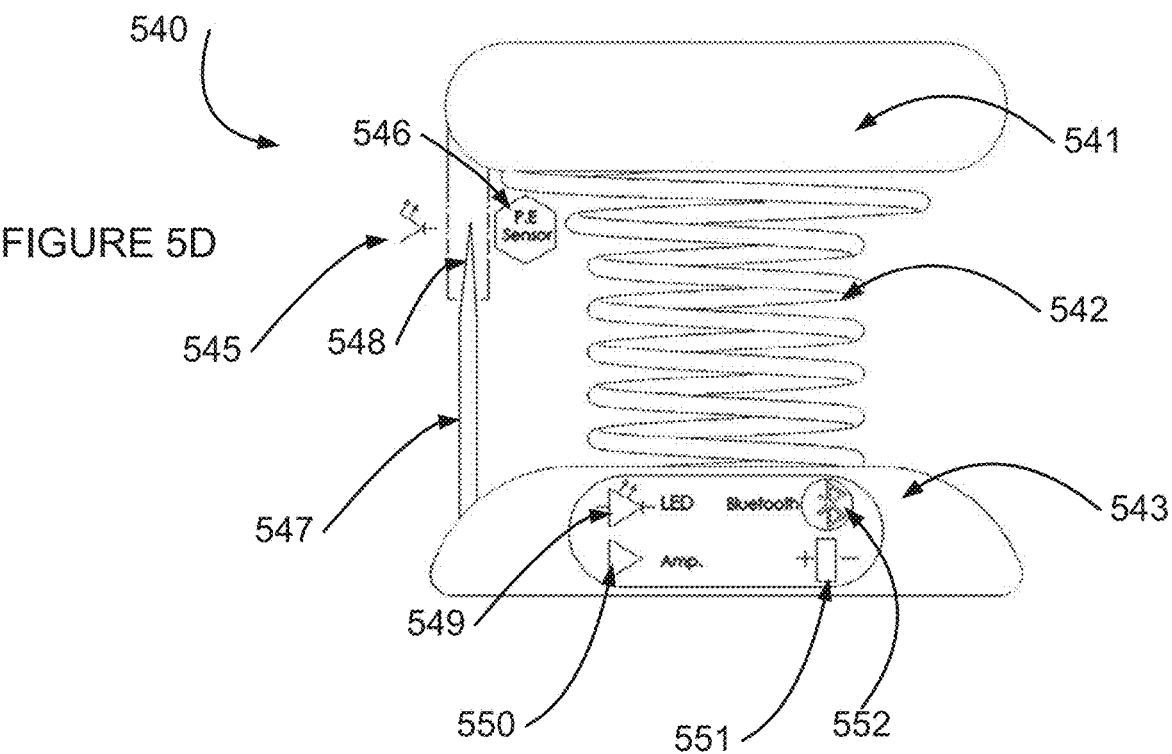
FIG. 5D is a simplified illustration of a device for retarding birth according to yet another example embodiment of the invention.

Reference is now made to FIG. 5D, which is a simplified illustration of a device 540 for retarding birth according to yet another example embodiment of the invention.

FIG. 5D depicts the device 540, the upper ring 541, the elastic component 542 and the lower ring 543.

In example embodiments depicted by FIG. 5D, the device 540 includes electrical components for measuring at least some of the above-mentioned birth progress parameters.

In some embodiments the device 540 optionally includes a Printed Circuit Board with at least some of the electrical components connected thereto.

In some embodiments the device 540 optionally includes a battery 551.

In some embodiments the device 540 optionally includes an RF communication device 552.

In some embodiments the device 540 optionally includes a contraction sensing component including a LED 545 and a photo-sensor 546 with a triangular slit 548 between them. Movement of the upper ring 541 and the anchoring element 543 cause different amounts of light to be blocked by the triangular slit 548, and detection of the light level in the photo-sensor 546 is optionally translated to a contraction magnitude.

In some embodiments the triangular slit 548 is a portion of a rod-like element 547 extending from the anchoring element 543 toward the upper ring 541.

In some example embodiments the devices 525 540 of FIGS. 5C and 5D are connected to a wire leading out of the vagina.

In some embodiments, power is supplied to the measuring components by wire, as is known in the art.

In some embodiments, measurements are relayed to a monitoring device external to the patient, as is known in the art.

Figure 5E:
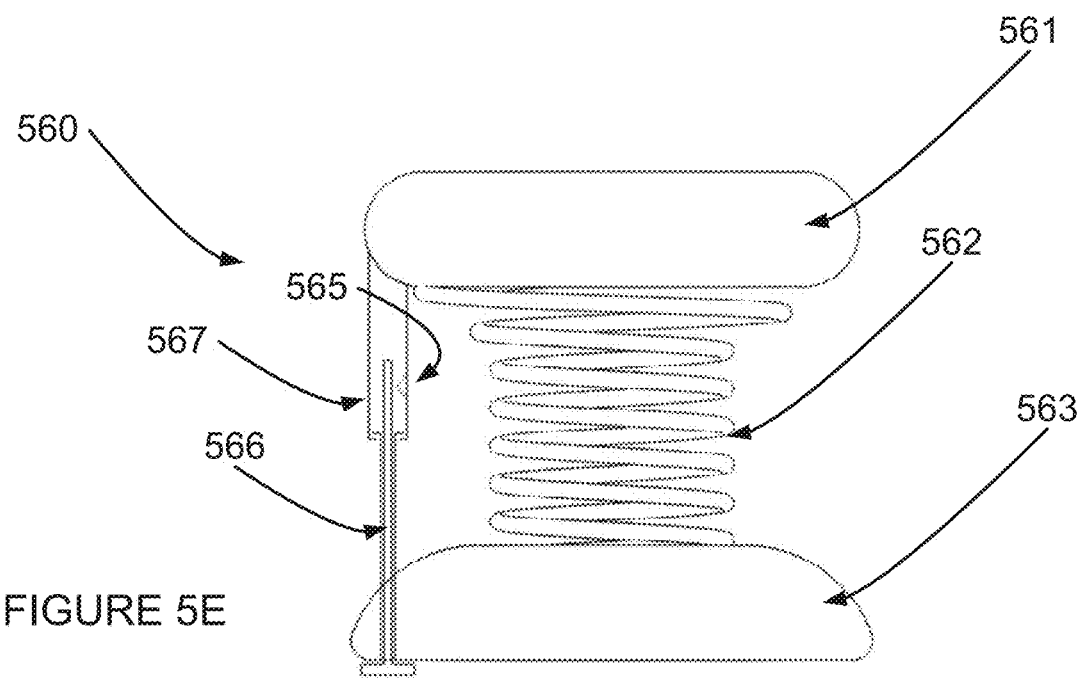
FIG. 5E is a simplified illustration of a device for retarding birth according to still another example embodiment of the invention.

Reference is now made to FIG. 5E, which is a simplified illustration of a device 560 for retarding birth according to still another example embodiment of the invention.

FIG. 5E depicts the device 560, the upper ring 561, the elastic component 562 and the lower ring 563.

In example embodiments depicted by FIG. 5E, the device 560 includes mechanical components for measuring at least some of the above-mentioned birth progress parameters.

In some embodiments, the device 560 tracks a maximum contraction.

The device 560 optionally includes a rod 566 for attaching to the lower ring 563, and a cylinder 567 including a scribing or marking tip 565 which scribes or marks the rod 566.

Movement of the upper ring 561 and the anchoring element 563 causes the tip 565 to mark on the rod 566.

In some embodiments a physician optionally removes the rod 566 easily or optionally the device 560 and optionally assesses the maximum contraction to date. The physician may then insert a fresh rod or may optionally insert the same rod or device 560 again.

In some embodiments a rod (not shown) is gradually pushed by the upper ring 561 through a non-reversing component (not shown) in the lower ring 563, such that the rod protrudes from the lower ring 563 but is not pulled back by the upper ring 561. A physician optionally inspects the protruding rod for assessing maximal contraction. In some embodiments the physician may release the non-reversing component and push the rod back onto the upper ring 561.

In some embodiments the device's change in dimensions during contraction is optionally measured by ultrasound and/or by a physical examination.

An Auto-Release Embodiment

In some embodiments the device, based on the maximum contraction force or the contraction frequency or the contraction forces, optionally automatically releases anchoring of the device to the cervix or vaginal wall.

In some embodiments the auto-release optionally causes a drop of the device out and through the vaginal canal.

In some embodiments the auto-release is optionally based on a monitoring process based on pressure and/or frequency of uterine contractions, optionally as described above in the section named "Measurement of birth progress parameters".

In some embodiments exceeding a certain threshold or a maximum contraction pressure and/or contraction frequency or contraction forces integral optionally releases the anchoring by cutting the wire that sutures the device to the cervix.

In some embodiments exceeding a certain threshold as described above will release the anchoring by un-inflating inflatable parts in the device.

A Drug Release Embodiment

In some embodiments the device is optionally used to release specific drugs appropriate to a specific stage in signs of birth progress.

Figure 5F:
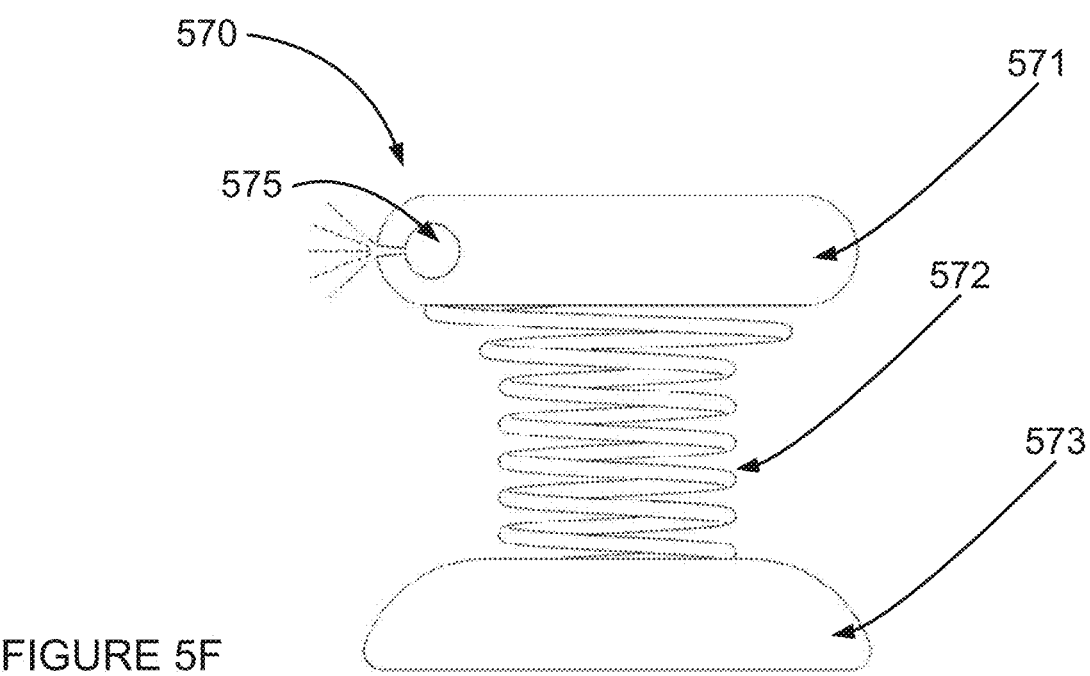
FIG. 5F is a simplified illustration of a device for retarding birth according to yet another example embodiment of the invention.

Reference is now made to FIG. 5F, which is a simplified illustration of a device 570 for retarding birth according to yet another example embodiment of the invention.

FIG. 5F depicts the device 570, the upper ring 571, the elastic component 572 and the lower ring 573.

A drug chamber 575 in the upper ring 571 optionally releases a drug to the vagina each time the pressure on the upper ring 571 of the device 570 exceeds a certain threshold.

In some embodiments the upper ring 571 includes a valve (not shown) which sets a pressure over which or under which the drug is released.

In some embodiments the drug delivery is via small holes in the upper ring 571.

In some embodiments the device infrastructure, optionally including the above-mentioned birth progress parameter measurements is optionally used to release specific drugs appropriate to a measured stage in signs of birth progress.

In some embodiments the drug release is optionally based on demand, such as in response to measuring contractions.

In some embodiments the drug release is optionally constant.

In some embodiments the drug release is controlled electronically, based, at least in part, on the electronic measurement of birth progress parameter measurements as described herein.

In some embodiments, the following are examples of drugs optionally intended for use:

Progesterone;
Pressolat;
Atosiban;
Indomed;
Magnesium;
Beta agonist;
other tocolytic drugs;
Oxytocin;
Prostaglandins; and
other drugs augmenting labor.

Figure 6:
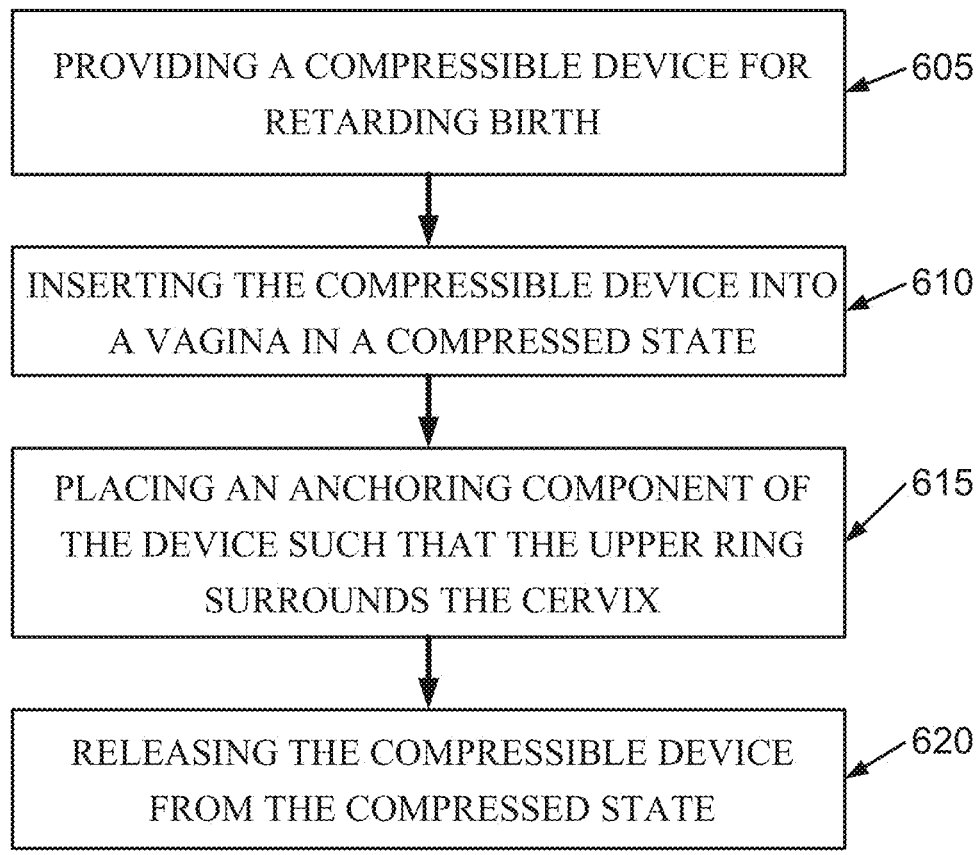
FIG. 6 is a simplified flowchart illustration of a method of inserting a device for retarding birth according to an example embodiment of the invention.

Reference is now made to FIG. 6, which is a simplified flowchart illustration of a method of inserting a device for retarding birth according to an example embodiment of the invention.

The method depicted by FIG. 6 includes:

providing a device for retarding birth (605) which comprises:

an upper ring for surrounding a cervix;
an anchoring component for anchoring the device; and
an elastic component for attaching the upper ring to the anchoring component, wherein the elastic component pushes the upper ring and the anchoring component apart;

inserting the device into a vagina in a compressed state (610) such that the upper ring and the anchoring component compress the elastic component;

placing the compressed device such that the upper ring surrounds the cervix (615); and releasing the device from the compressed state (620) such that the upper ring moves away from the anchoring component.

In some embodiments, following the insertion of the device into a vagina in a compressed state (610), the upper ring is placed at its target position, and the compression lock is released to allow the lower ring to lengthen along the cervix.

In some embodiments, following the insertion of the device into a vagina in a compressed state (610), the upper ring is placed at its target position, and the compression lock is released to allow the lower ring to lengthen along the cervix, and reach a position such that the lower ring surrounds the cervix.

Figure 7:
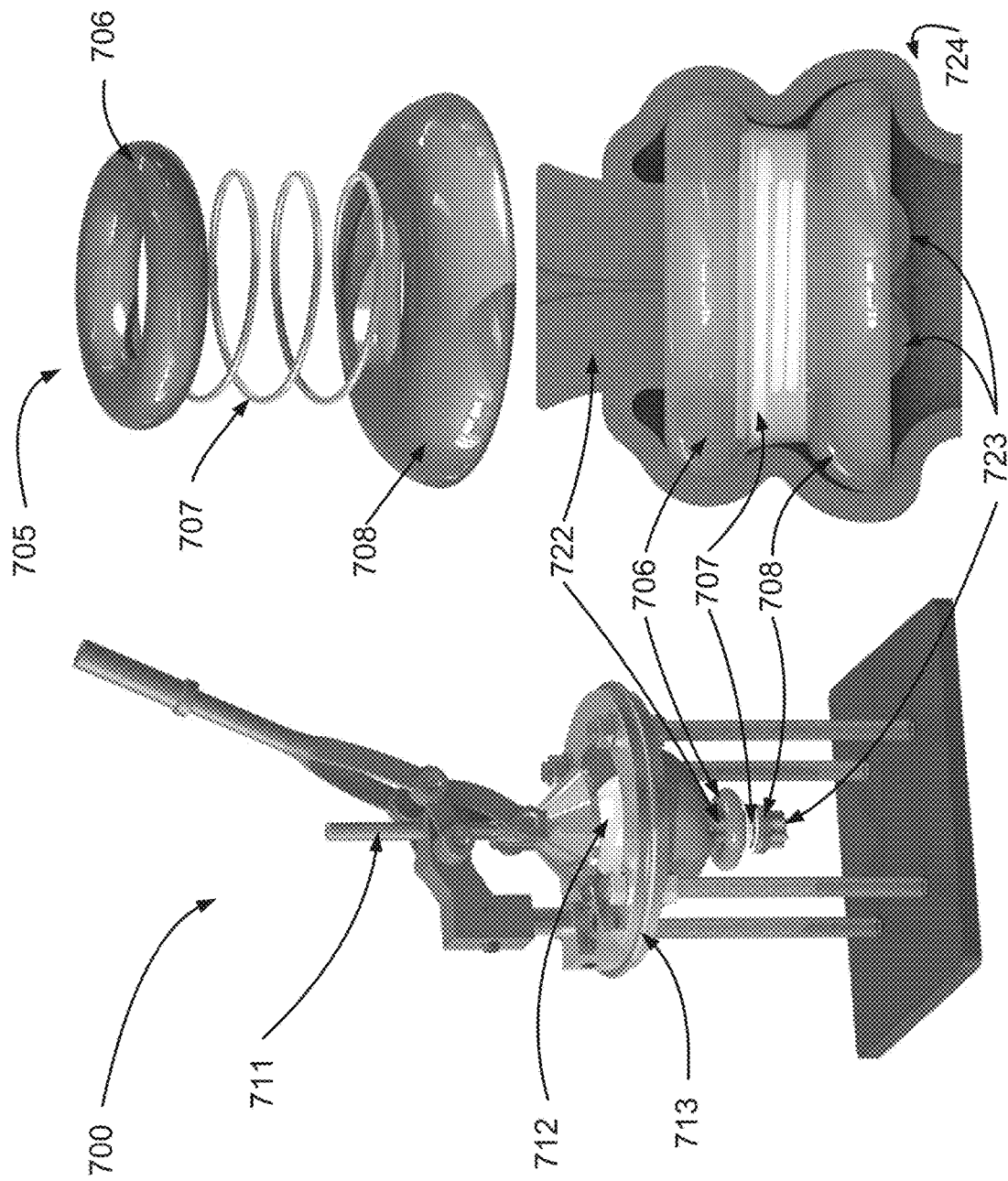
FIG. 7 is a simplified illustration of a first, testing device for testing a second device for retarding birth, according to an example embodiment of the invention.

Reference is now made to FIG. 7, which is a simplified illustration of a first, testing device for testing a second device for retarding birth, according to an example embodiment of the invention.

FIG. 7 depicts a press 700 as an example embodiment of the first testing device, designed for pressing a model 712 of an amniotic sac with a fetus or with a fetus' head, or of a fetus, or of a fetus head through a model of a cervix 722.

In some embodiments the model of the cervix 722 may include a model of a portion of a vagina 724.

In some embodiments the press 700 includes a frame for attaching the model of the cervix 722.

Additional Description

The following includes an additional description of example embodiments of the invention.

In some embodiments, a device situated on the cervix, under the internal os, aimed at stabilizing the cervix and safely absorbing the forces of contractions. This is potentially achieved by redirecting the forces and pressure vectors and dissipating energy on a large surface of the cervix, and/or vaginal wall and/or pelvic bones and/or on the device. The device potentially enables tissue to resist and postpone dilation and effacement of the cervix and thus prevent or delay preterm birth due to premature contractions or cervical insufficiency or other indications (FIG. 3 and reference 705 of FIG. 7).

A Bench Test

A bench test device for evaluating a pre-term birth delaying device is depicted in FIG. 7.

In some embodiments, the test device will measure an amount of pressure the pre-term birth delaying device can absorb safely in mm Hg units.

The test device is optionally made of a rigid steel frame with a lever mechanism activated by weight to deliver stress, and optionally a silicone sleeve to mimic the cervix. A ball is optionally contained inside a bag filled with saline to mimic a fetal head in an amniotic sac. Different diameter size balls are optionally used to mimic fetuses at different weights and different gestational ages. The lever optionally pushes the ball and the saline bag. The model cervix diameter is dilated as a result of the vector of forces.

The pre-term birth delaying device is optionally anchored to the silicone cervix, transforming the force direction to a normal direction of the tangent point of contact of the upper ring, stress in the normal direction to the lower ring, compression of the elastic element between them and friction along the device resulting in lower normal force on anchoring circumference: E contraction=$E_N + E_{tg} + E_\mu + S_k$.

Some Data

A feasibility research has been performed and has shown successful results (FIG. 3 and FIG. 7). A device including an upper and lower ring and an elastic mechanism such as a spring or a damper connecting between them was produced. The elastic object behaves as a shock absorber to smooth out, store or damp shock impulses and dissipate energy applied by the forces of uterine contractions. The device is optionally positioned inside the vagina surrounding the cervix.

In some embodiments the lower ring is optionally supported and anchored in place by internal body pressure applied by the vaginal wall and the pelvic bones.

In some embodiments installation of the device is achieved by inserting the device while the elastic object is locked in a compressed mode, placing the lower ring at its target position and gradually releasing the compression lock to allow the top ring elevate towards the fornix. In some embodiments installation of the device is achieved by inserting the device while the elastic object is locked in a compressed mode, placing the top ring at its target position and gradually releasing the compression lock to allow the lower ring to descend towards the vagina. In some embodiments the mechanism of releasing the lock optionally gives control over the final length of the elastic intermediate and also optionally its orientation to fit the curvature of the cervix.

In some embodiments the upper ring acts as a cuff holding on to a cross section of the cervix below the internal os.

During contractions, the device enables a vector change of the applied force and pressure and dissipates them on a larger surface of the cervix so as to potentially enable the tissue to resist stress, dilatation and shortening of the cervix at a given time, potentially without adding physical restrictions which may result in ischemia, atrophy or rupture. A portion of the energy is transferred through the anchored lower ring to the vaginal wall and pelvic bones. When a contractions ends, the device pushes the top ring back into the fornix, providing a high circumferential support.

In some embodiments the device also includes a feedback mechanism to optionally measure contraction pressure and frequency, amongst other parameters. The elastic object of the device is compressed and decompressed during contractions resulting in a change of length, diameter and inclination, and achieves high quality readings which are measured.

In some embodiments the measurements are performed by a mechanical configuration.

In some embodiments the measurements are performed by an electronic configuration.

Figure 8B:
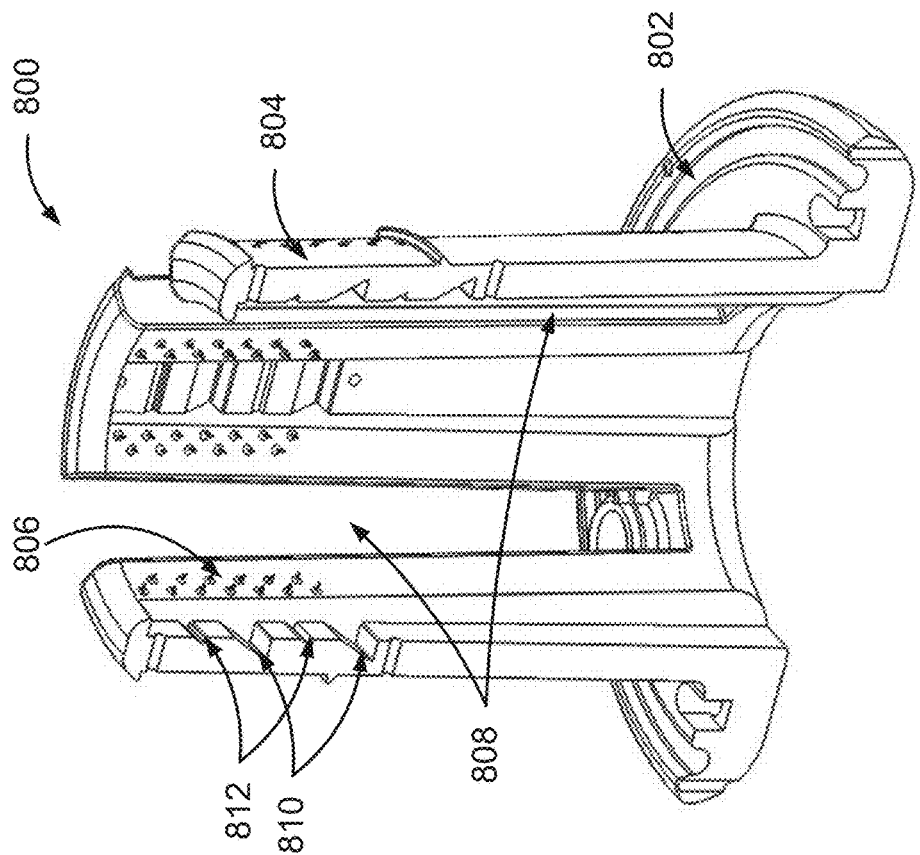
FIGS. 8A and 8B are simplified illustrations of a portion of an anchoring component of a device for retarding birth according to still another example embodiment of the invention.
Figure 8A:
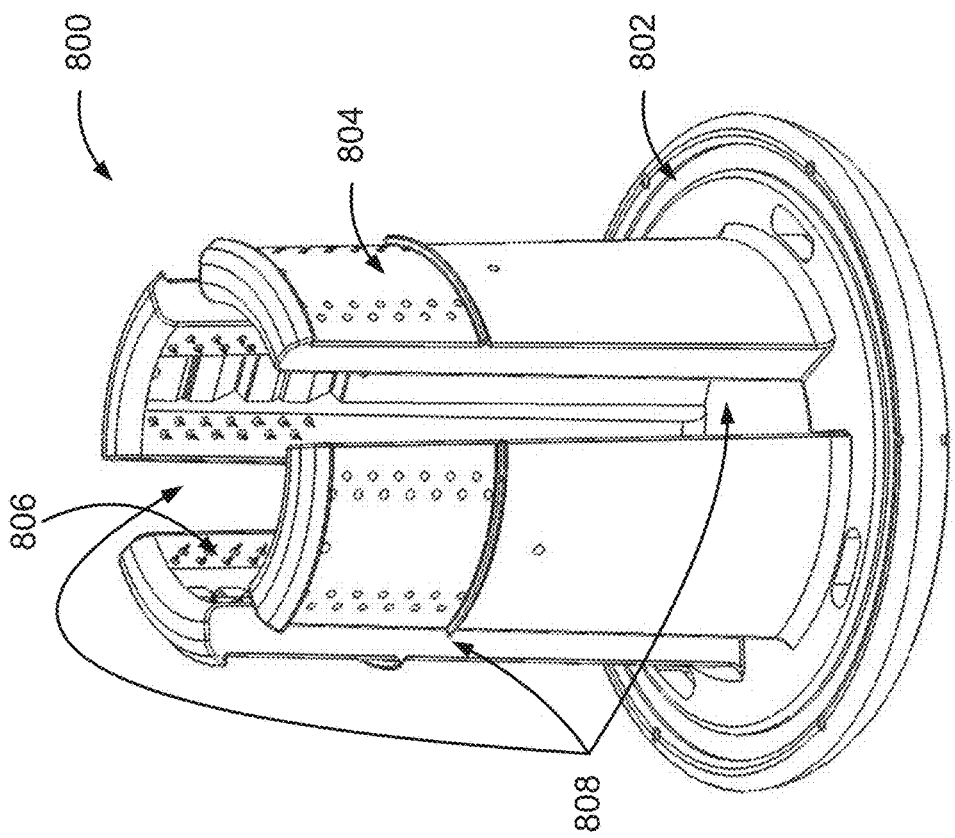

Reference is now made to FIGS. 8A and 8B, which are simplified illustrations of a portion of an anchoring component 800 of a device for retarding birth according to still another example embodiment of the invention.

FIG. 8A is an isometric view of the portion of the anchoring component 800, and FIG. 8B is an isometric view of a cross section of the portion of the anchoring component 800.

The anchoring component 800 includes a lower ring 802, lower from a caretaker's point of view, that is, toward a vaginal side, opposite a uterus side. The anchoring component 800 also includes an anchoring extension 804 for surrounding a cervix (not shown). The anchoring extension 804 includes many projections 806 which are optionally used to increase friction between the anchoring extension 804 and the cervix, anchoring the device to the cervix and potentially preventing the device from slipping along the cervix.

In some embodiments the projections 806 are sharp and pin like.

In some embodiments the projections 806 are bristles, or bristle-like.

In some embodiments tips of the projections 806 are approximately perpendicular to an inner surface of the anchoring extension 804.

In some embodiments tips of the projections 806 are inclined at an angle toward the lower ring 802.

In some embodiments the anchoring extension 804 includes slits 808 as shown in FIGS. 8A and 8B, which potentially enable the anchoring extension 804 to flexibly open—enabling the anchoring extension 804 to slip along the cervix, and close—enabling the anchoring extension 804 to grip the cervix.

In some embodiments the anchoring extension 804 may be flexible yet without the slits 808 shown in FIGS. 8A and 8B, and still potentially enable the anchoring extension 804 to flexibly open—enabling the anchoring extension 804 to slip along the cervix, and close—enabling the anchoring extension 804 to grip the cervix.

In some embodiments the anchoring extension 804 includes a set of shallow depressions 812 as shown in FIGS. 8A and 8B and deeper depressions 810 as measured from an inside of the anchoring extension 804.

Figure 8D:
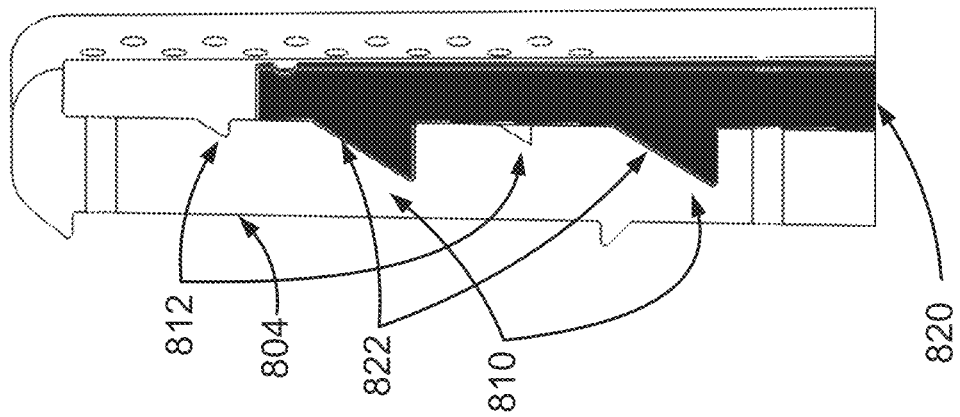
FIGS. 8C and 8D are simplified illustrations of the anchoring extension and of a latch of the anchoring component of FIGS. 8A and 8B.
Figure 8C:
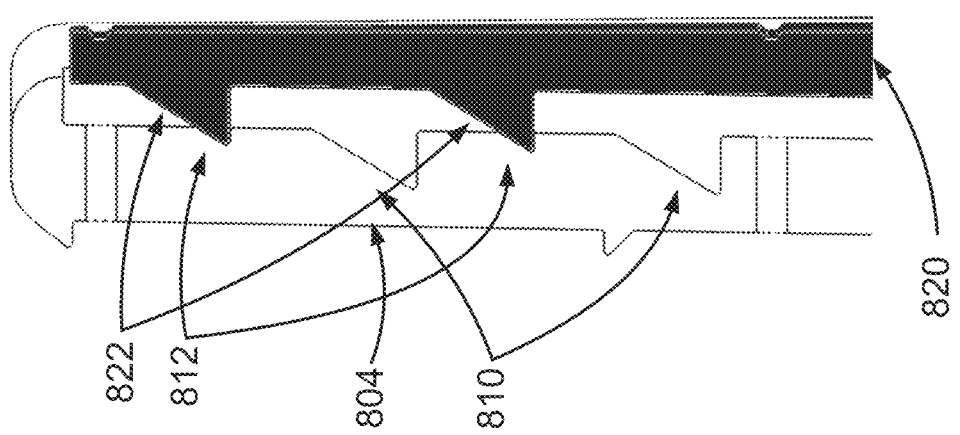

The depressions fit compatible protrusions in one or more latches (not shown in FIGS. 8A and 8B, but shown in FIGS. 8C and 8D).

In some embodiments ventilation holes are included in the anchoring extension 804, potentially enabling fluid discharge.

Reference is now made to FIGS. 8C and 8D, which are simplified illustrations of the anchoring extension 804 and of a latch 820 of the anchoring component 800 of FIGS. 8A and 8B.

The one or more latches 820 may potentially be set at two different states.

In a first state, depicted in FIG. 8C, protrusions 822 of the latches fit into the shallow depressions 812, potentially pushing on the anchoring extension 804 to flex away from the cervix, potentially concealing the projections 806 of FIGS. 8A and 8B in holes in the latch 820 and preventing the projections 806 of FIGS. 8A and 8B from engaging the cervix.

In a second state the protrusions 822 of the latches fit into the deeper depressions 810, potentially allowing the anchoring extension 804 to flex closer to the cervix, potentially exposing tips of the projections 806 jutting from the holes in the latch and allowing the projections 806 of FIGS. 8A and 8B to engage the cervix.

In some embodiments the device, a user may optionally switch an anchoring component from the state depicted in FIG. 8D to the state depicted in FIG. 8C, or vice versa, from a state where the projections 806 are exposed to a state where the projections 806 are hidden. This potentially enables a quick release mechanism of the device.

In some embodiments, the projections 806 of FIGS. 8A and 8B are on the anchoring extension 804 of FIGS. 8A and 8B, and the latch 820 of FIGS. 8C and 8D serves to switch the anchoring extension from concealing to exposing the projections 806 of FIGS. 8A and 8B.

In some embodiments, the projections 806 of FIGS. 8A and 8B are on the latch 820 of FIGS. 8C and 8D, and the latch 820 serves to switch the anchoring extension from concealing to exposing the projections 806 of FIGS. 8A and 8B.

Figure 8E:
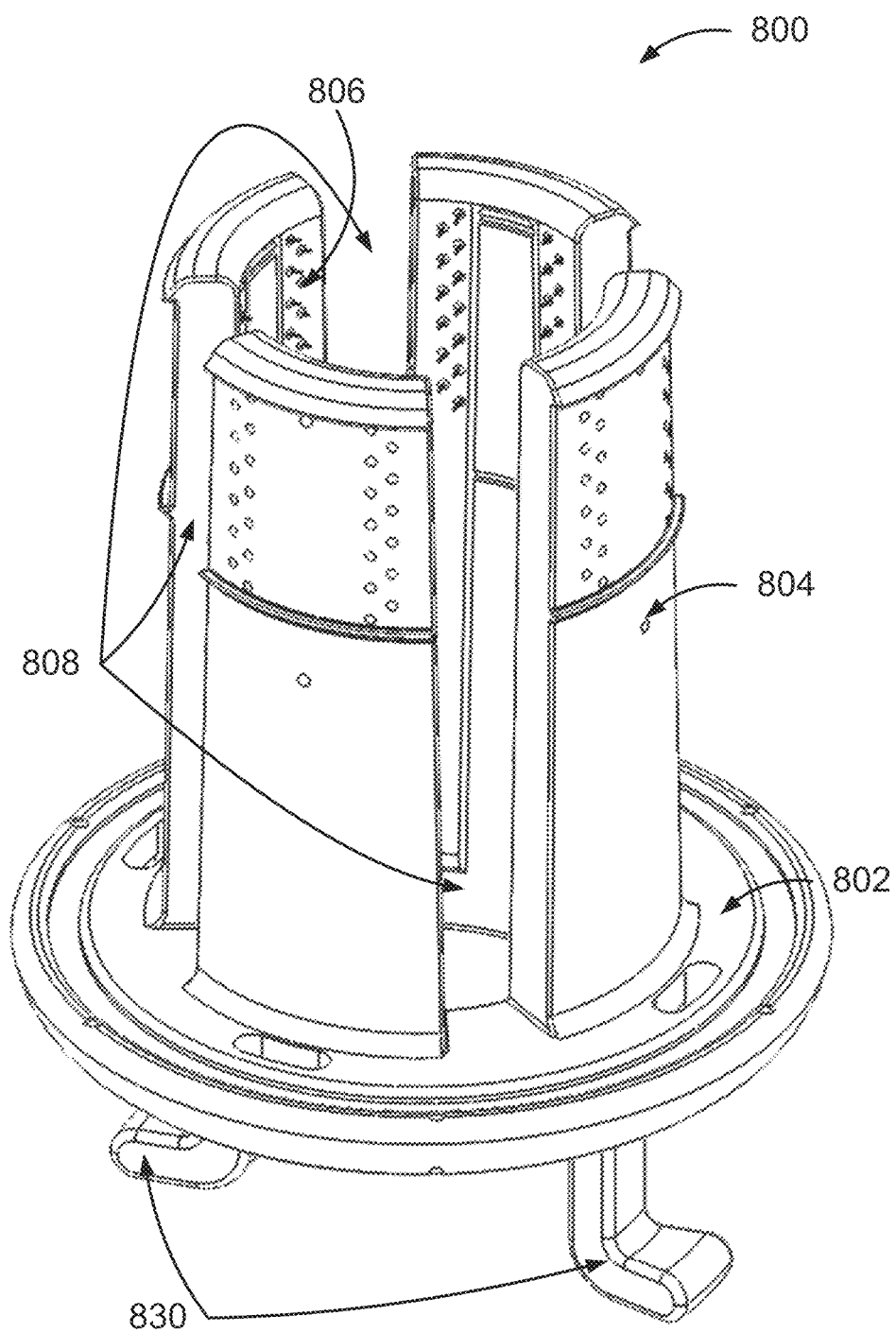
FIG. 8E is another simplified illustration of the anchoring component of FIGS. 8A and 8B.

Reference is now made to FIG. 8E, which is another simplified illustration of the anchoring component 800 of FIGS. 8A and 8B.

FIG. 8E is an isometric view of the lower ring 802 and the anchoring extension 804 with the slits 808 and projections 806. FIG. 8E adds a view of handles 830 attached to the latches 820 of FIGS. 8C and 8D. The handles potentially enable a caretaker to switch the anchoring component 800 from the state depicted in FIG. 8C to the state depicted in FIG. 8D, that is, from a state where the projections 806 are hidden to a state where the projections 806 are exposed. This optionally enables a quick release mechanism for the device.

A Quick-Release Embodiment

In some embodiments the device, a user may optionally use a component such as the handles 830 to switch the anchoring component 800 from the state depicted in FIG. 8D to the state depicted in FIG. 8C, that is, from a state where the projections 806 are exposed to a state where the projections 806 are hidden. This potentially enables a quick release mechanism of the device.

Reference is now made to FIGS. 9A and 9B, which are simplified illustrations of a device 1000 using the anchoring component 800 of FIGS. 8A-8E.

FIG. 9A is an isometric view of the device 1000, and FIG. 9B is an isometric view of a cross section of the device 1000.

FIGS. 9A and 9B depict the lower ring 802 of the anchoring component 800 of FIGS. 8A and 8B, the anchoring extension 804 of the anchoring component 800, the handle 830 of the latch 820 of the anchoring component 800 of FIGS. 8A and 8B, an upper ring 1002, and an elastic component 1004.

Figure 9D:
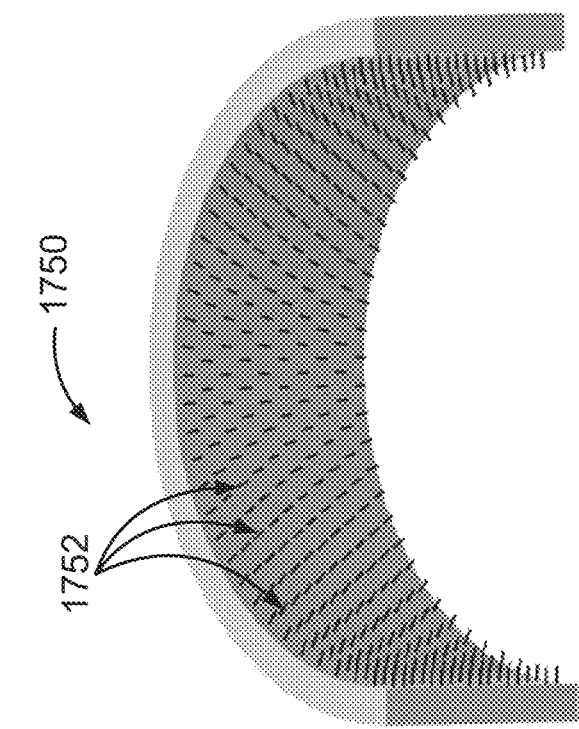
FIGS. 9C and 9D are simplified illustrations of example embodiments of anchoring extensions.
Figure 9C:
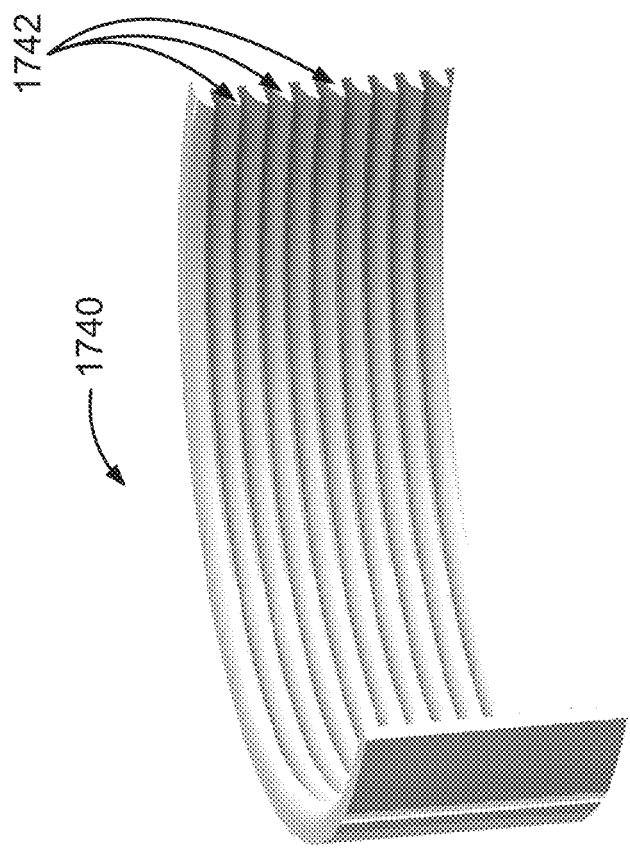

Reference is now made to FIGS. 9C and 9D, which are simplified illustrations of example embodiments of anchoring extensions.

FIG. 9C is an isometric view of a cross-section of an anchoring extension 1740, including circular or semi-circular protrusions 1742 for increasing friction between the anchoring extension 1740 and a surface of a cervix against which the anchoring extension 1740 is placed.

FIG. 9D is an isometric view of a cross-section of an anchoring extension 1750, including many sharp, or pin-like, or bristle-like protrusions 1752 for increasing friction between the anchoring extension 1750 and a surface of a cervix against which the anchoring extension 1750 is placed.

Some potential benefits of using anchoring extensions include:

In some embodiments, no suture is required, and the device is easily and simply deployed, potentially without anesthesia, and potentially in an out-patient or clinic procedure. In no-suture embodiments, a quick release mechanism may optionally be used to detach the device from a cervix and remove the device from the vagina.

In some embodiments, suturing is optionally used, but less suturing may be required, potentially resulting in a simpler procedure, potentially resulting in less damage to the sutured organ, and potentially resulting in better device retention.

Figure 10A:
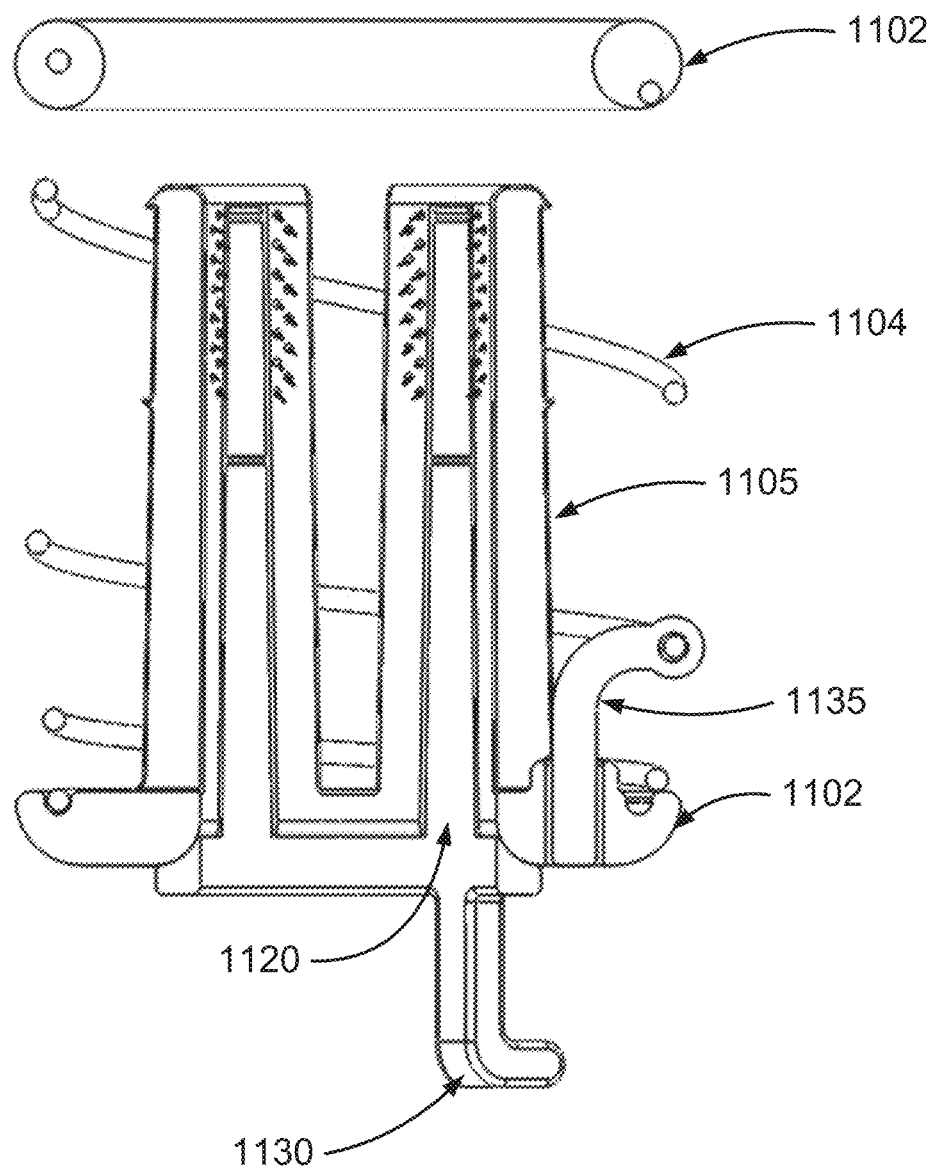
FIG. 10A is a simplified illustration of yet another example embodiment of the invention.

Reference is now made to FIG. 10A, which is a simplified illustration of yet another example embodiment of the invention.

FIG. 10A illustrates a handle 1130 for manipulating a latch 1120, and a gauge 1135 for estimating a force at which the upper ring is pushing toward the lower ring.

FIG. 10A is a cross-sectional illustration depicting a lower ring 1102 of an anchoring component, a tube 1105 of an anchoring component, the handle 1130 of the latch 1120 of an anchoring component, an upper ring 1102, and an elastic component 1104. FIG. 10A also depicts the optional gauge 1135, attached to the elastic component 1104 and protruding through a hole in the lower ring 1102.

In some embodiments the gauge 1135 potentially enables a caretaker to feel how much the elastic component 1104 is compressed, by optionally feeling how much the gauge 1135 protrudes through the hole in the proximal ring 1102.

In some embodiments the gauge 1135 potentially enables a caretaker to serve as a pressure indicator for the caretaker to set an initial pressure on the fornix.

In some embodiments the gauge 1135 potentially provides a physician an indication if the upper ring is too pressed up against the fornix, also termed preload. A contraction of the elastic element, or spring, optionally compresses its coils, optionally pushing the gauge which the coil may be connected to, optionally resulting in pushing the gauge past a baseline location, for example a bottom face of the lower ring, optionally resulting in a measurable indication of force applied on the fornix. Some non-limiting examples of translating a protrusion of the gauge past the baseline to force include using a look-up table or a chart prepared for the gauge which correlates protrusion to force; marking the gauge with slits or protrusions which, when aligned with the baseline, correspond to specific known forces.

In some embodiments checking the gauge is optionally performed upon installation of the device, and in some embodiments upon optionally performing check-ups.

In some embodiments the gauge uses three components of the device: a lower base, for example the lower ring, to serve as a cam and/or as a reference point of measurement; A spring or elastic component that reacts to pressure by changing its length; and an upper ring to push against the fornix, transforming an applied pressure to spring compression.

In some embodiments installation of the device is optionally achieved by inserting the device while the elastic component is optionally compressed by tying through key holes in the lower ring, and/or tying to the anchoring extension depicted in FIGS. 8A-8E.

In some embodiments installation of the device is optionally achieved by inserting the device while the anchoring extensions are tied to the spring coil in order to dilate the anchoring extensions at an angle at the device's distal part so the device can slide smoothly on the cervix.

In some embodiments, once the device is in place, that is, the cervix is inside the device, the tying is removed and the latch of the anchoring extension is pushed a step to expose anchoring bristles and anchor the device against the cervix.

In some embodiments, when the device is in place and it is desired to remove the device, the latch is pushed in an opposite direction of to the installation direction, in order to detach and conceal the anchoring bristles from the cervix, and the device is pulled out of the vagina.

Figure 10C:
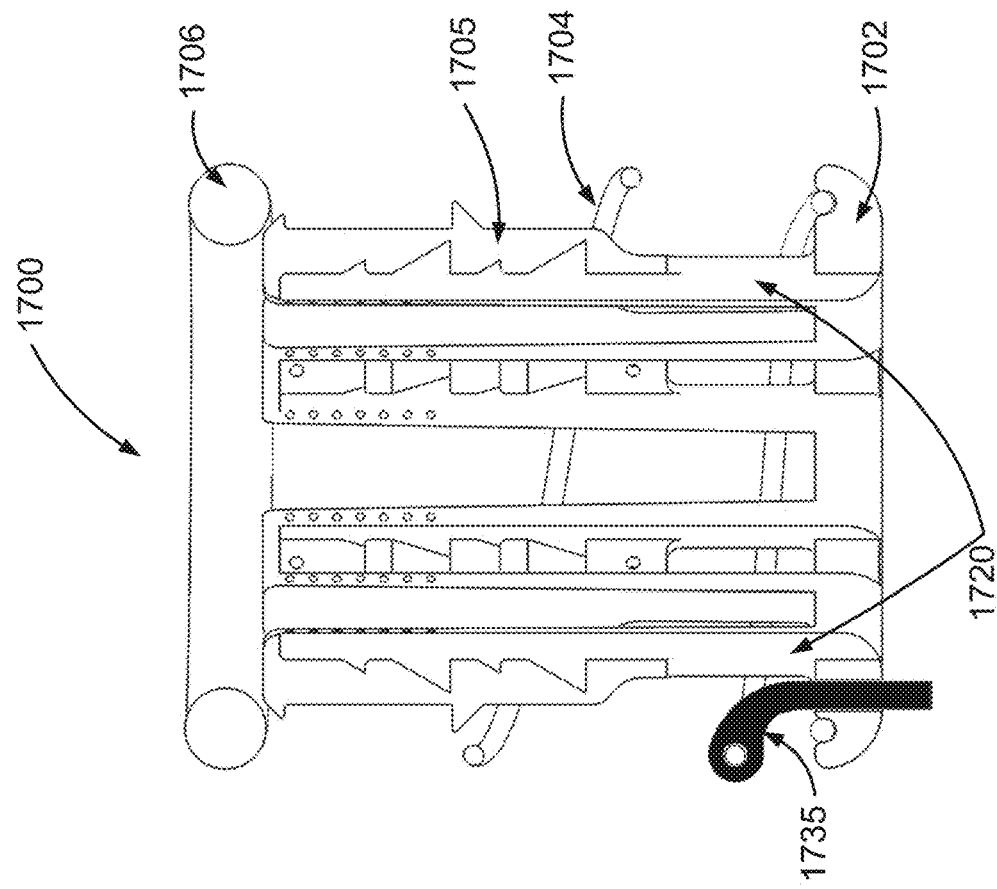
FIGS. 10B and 10C are simplified illustrations of still another example embodiment of the invention, in a relaxed state (FIG. 10B) and in a contracted state (FIG. 10C)
Figure 10B:
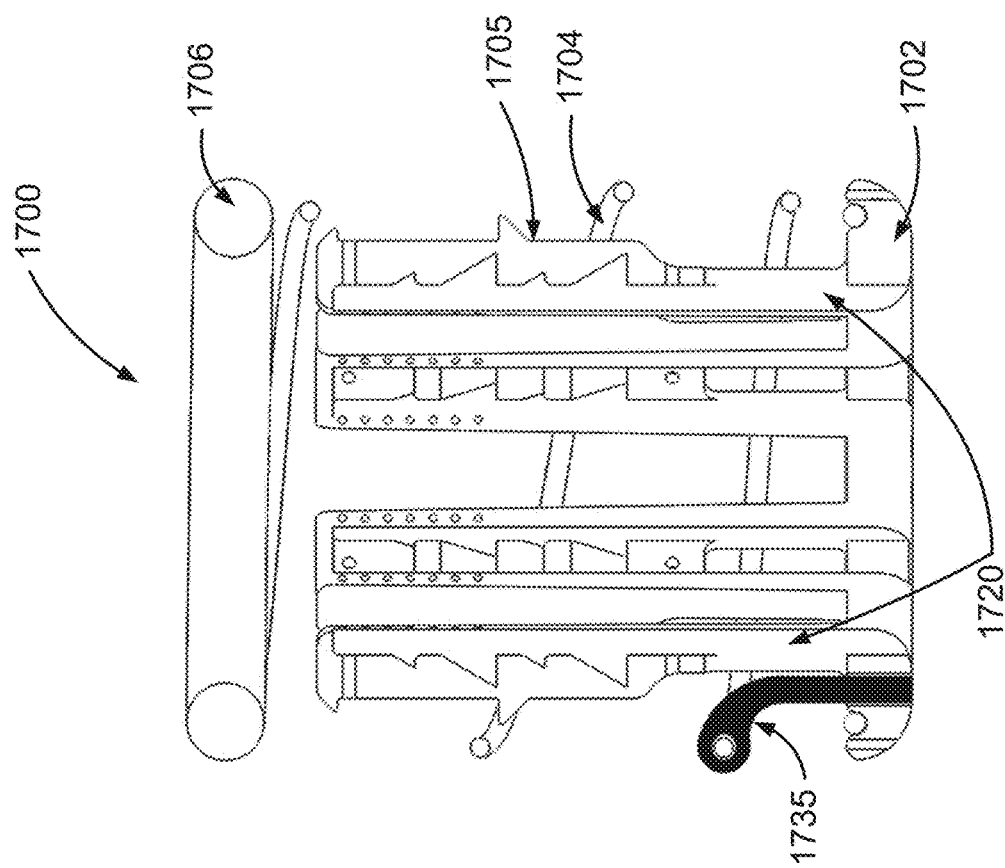

Reference is now made to FIGS. 10B and 10C, which are simplified illustrations of still another example embodiment 1700 of the invention, in a relaxed state (FIG. 10B) and in a contracted state (FIG. 10C).

FIGS. 10B and 10C depict a protrusion of a gauge from a bottom ring, enabling a physician to estimate a force at which the upper ring is pushing toward the lower ring.

FIGS. 10B and 10C depict cross-sectional illustrations of a lower ring 1702 of an anchoring component, an anchoring extension 1705 of an anchoring component, a latch 1720 of an anchoring component, an upper ring 1706, and an elastic component 1704. FIGS. 10A and 10B also depict an optional gauge 1735, attached to the elastic component 1704 and placed in a hole in the lower ring 1702.

FIG. 10B depicts the example embodiment 1700 in a relaxed state, and the gauge 1735 does not protrude from the lower ring 1702.

FIG. 10C depicts the example embodiment 1700 in a contracted state, and the gauge 1735 does protrude from the lower ring 1702.

Figure 10D:
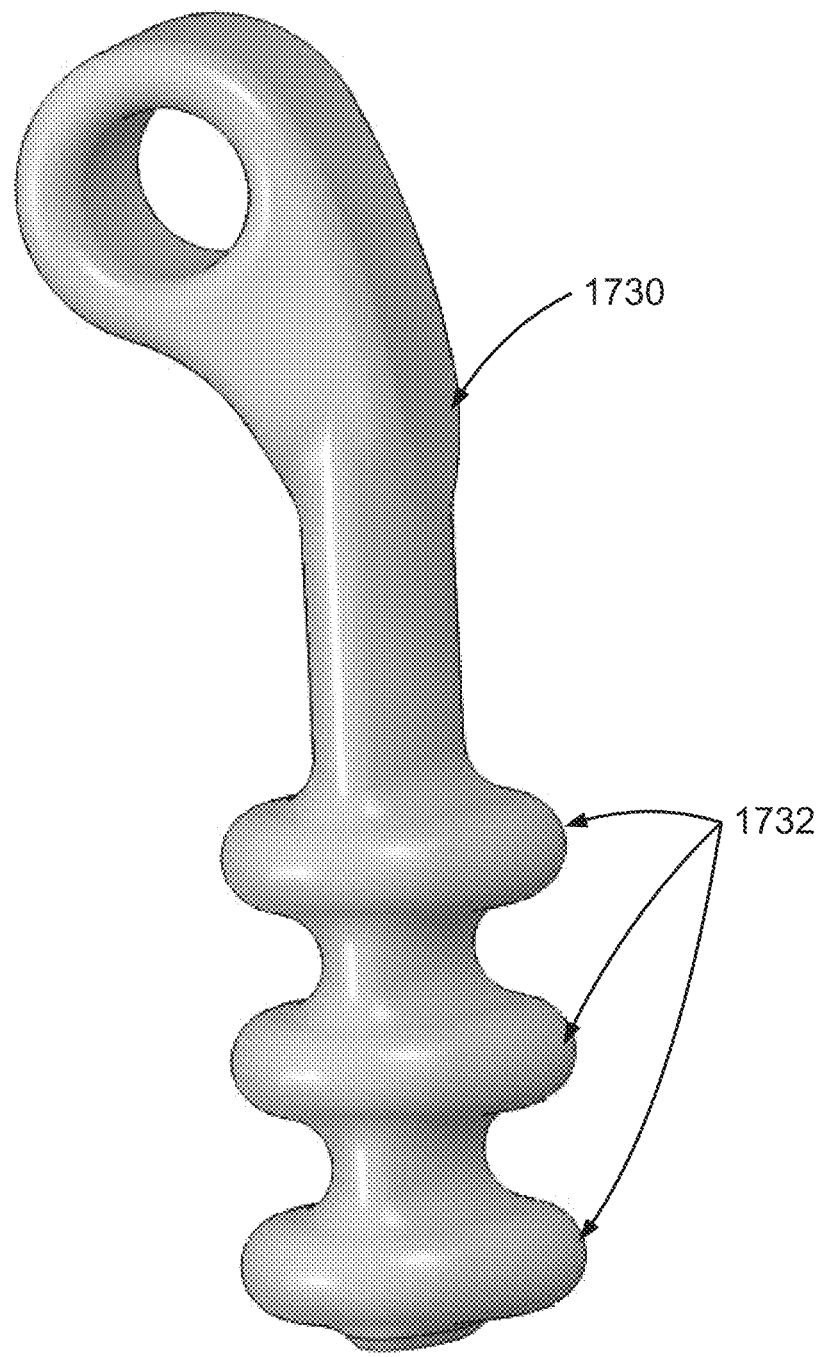
FIG. 10D is a simplified illustration of an example embodiment of a gauge.

Reference is now made to FIG. 10D, which is a simplified illustration of an example embodiment of a gauge 1730.

The gauge 1730 depicts an example embodiment having three protrusions 1732 from a distal end of the gauge 1730. The protrusions 1732 potentially enable a physician to feel by how much the gauge protrudes from the lower ring (not shown), potentially even with a gloved hand.

In some embodiments, by estimating by how much the gauge protrudes from the lower ring the physician may estimate a change in length of the device, thereby potentially estimating pressure on the device.

In some embodiments, by estimating pressure on the device, the physician may tell if the device exerts a desired pressure on the fornix.

In some embodiments, by estimating pressure on the device, the physician may tell pressure of a contraction of the uterus.

Figure 11A:
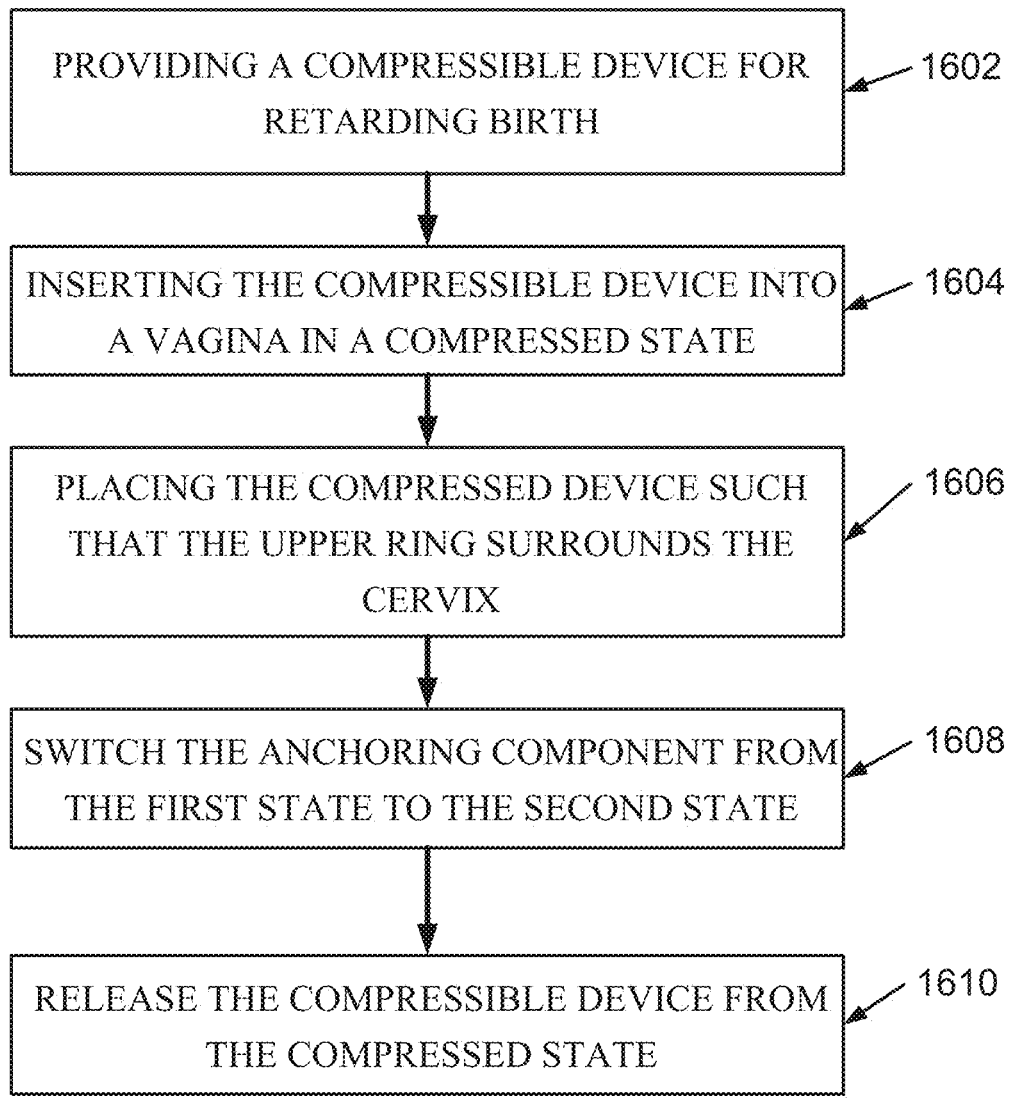
FIG. 11A is a simplified flowchart illustration of a method of inserting a device for retarding birth according to another example embodiment of the invention.

Reference is now made to FIG. 11A, which is a simplified flowchart illustration of a method of inserting a device for retarding birth according to another example embodiment of the invention.

The method depicted by FIG. 11A includes:

providing a device for retarding birth (1602), which includes:
- an upper ring for surrounding a cervix;
- an anchoring component for anchoring the device, the anchoring component comprising an anchoring extension comprising projections arranged to be in one of two states: a first state in which the projections are concealed from a surface of the cervix, and a second state in which the projections are exposed to the surface of the cervix; and
- an elastic component for attaching the upper ring to the anchoring component, wherein the elastic component pushes the upper ring and the anchoring component apart;

inserting the device into a vagina in a compressed state (1604), such that the upper ring and the anchoring component compress the elastic component;

placing the compressed device such that the upper ring surrounds the cervix (1606); and switching the anchoring component from the first state to the second state (1808), such that the projections are exposed to the surface of the cervix, thereby anchoring the device against the cervix; and releasing the device from the compressed state (1610), such that the upper ring moves away from the anchoring component.

Figure 11B:
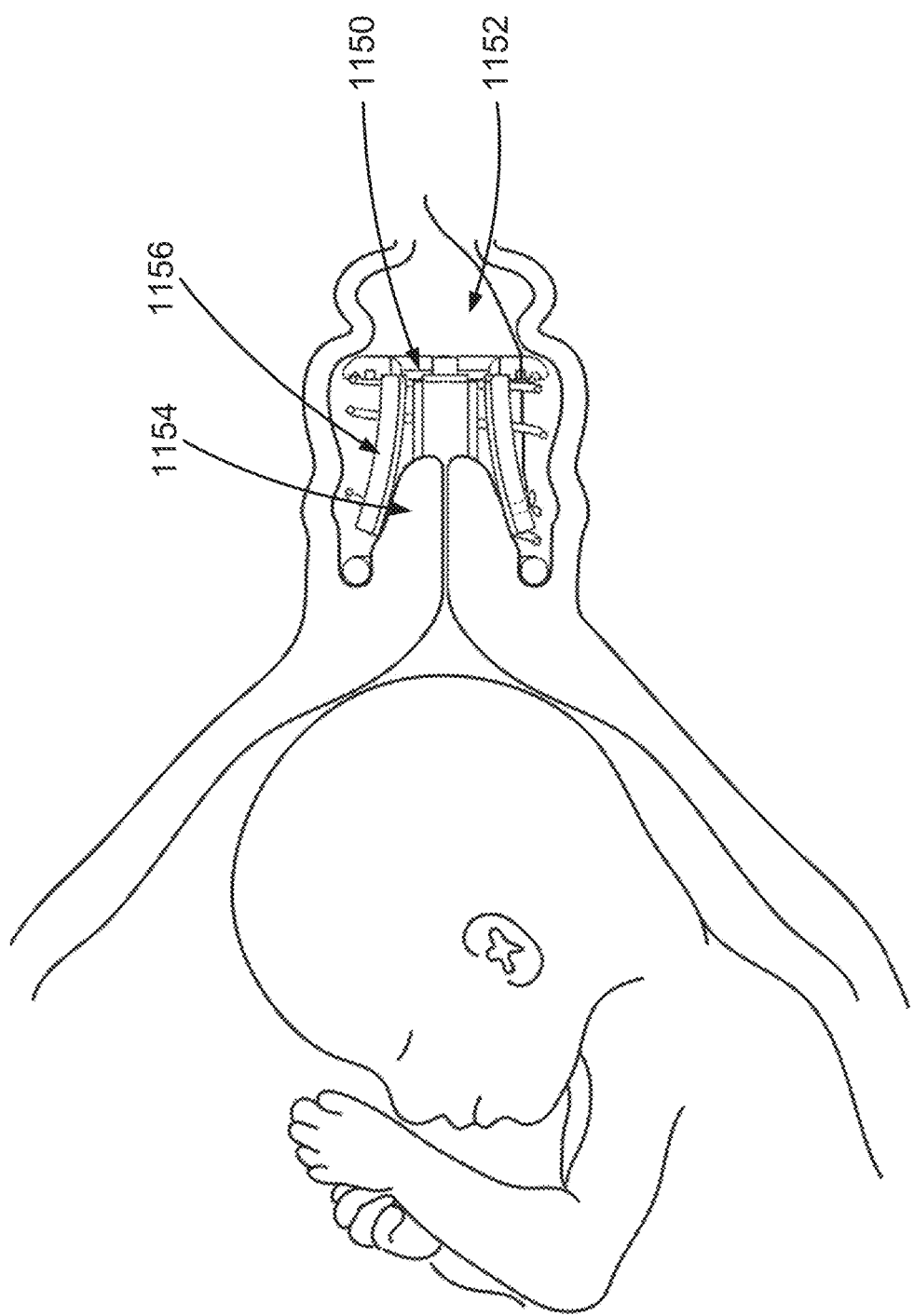
FIG. 11B is a simplified illustration of an example embodiment of the invention inserted into a vagina and around the cervix.

Reference is now made to FIG. 11B, which is a simplified illustration of an example embodiment 1150 of the invention inserted into a vagina 1152 and around the cervix 1154.

FIG. 11B depicts an anchoring tube 1156 expanding to surround the cervix 1154.

Figure 12B:
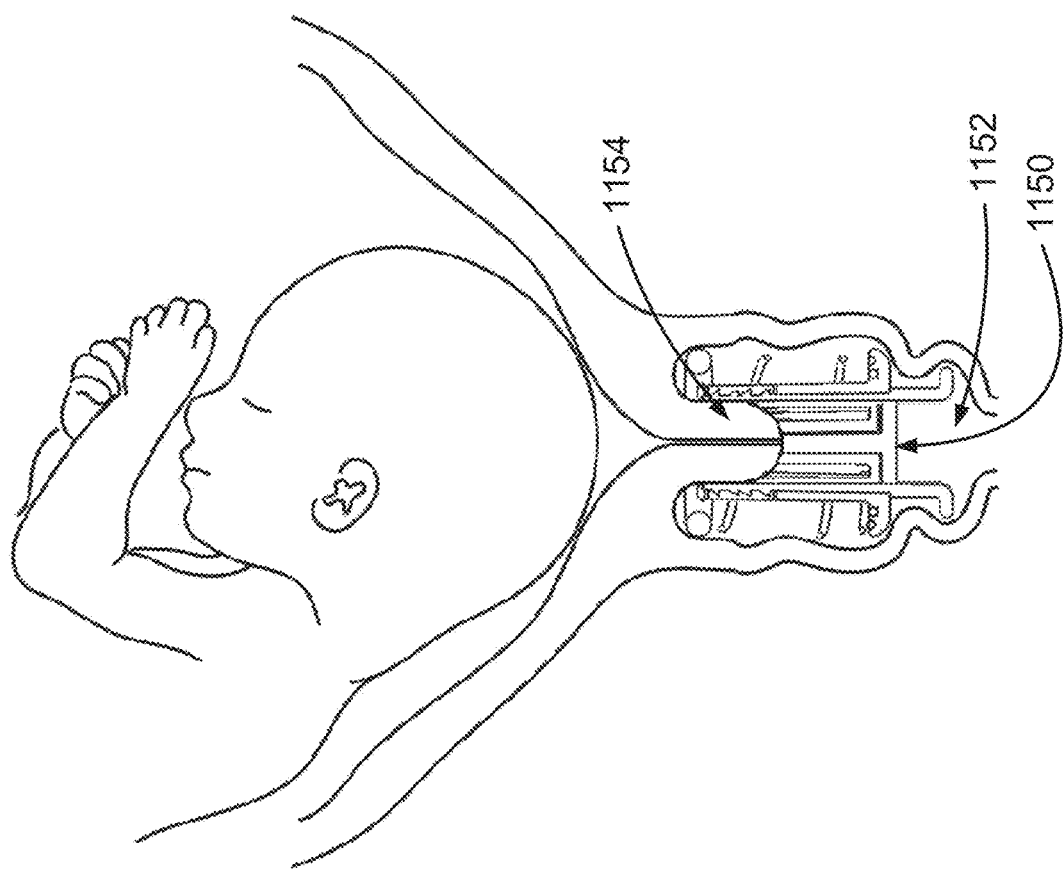
FIG. 12B is a simplified illustration of the example embodiment of FIG. 12B within the vagina and around the cervix, when the uterus is contracted and the cervix temporarily dilates and shortens.
Figure 12A:
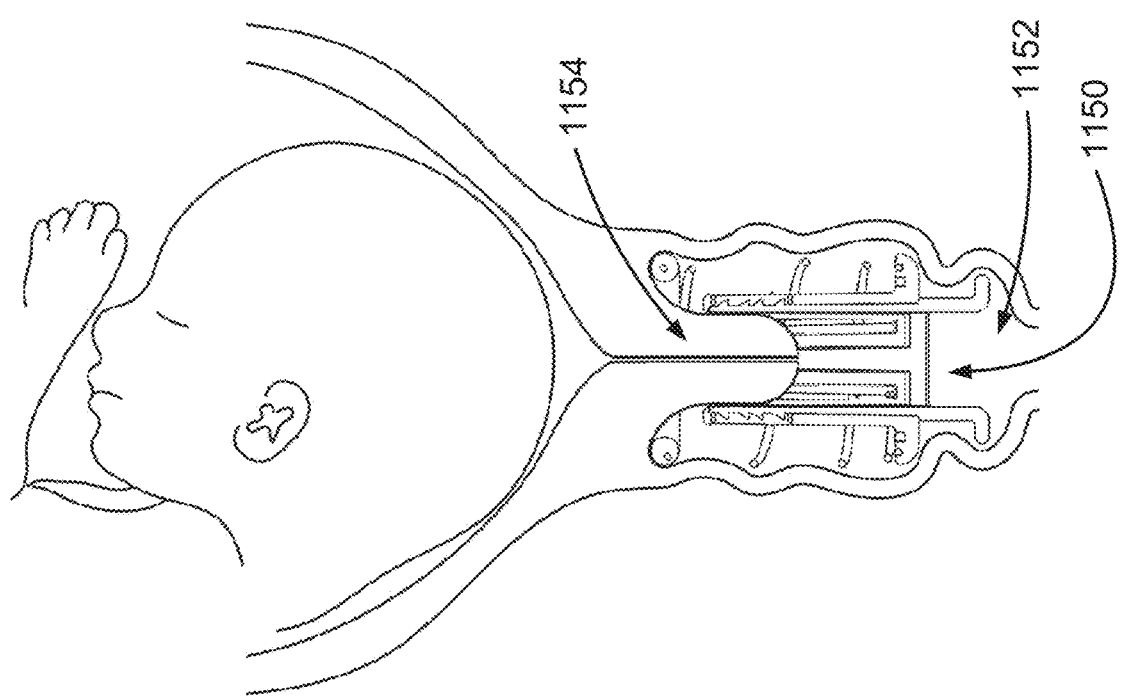
FIG. 12A is a simplified illustration of an example embodiment of the invention within the vagina and around the cervix, when the uterus is not contracted.

Reference is now made to FIG. 12A, which is a simplified illustration of an example embodiment 1150 of the invention within the vagina 1152 and around the cervix 1154, when the uterus is not contracted.

Reference is now made to FIG. 12B, which is a simplified illustration of the example embodiment 1150 of FIG. 12B within the vagina 1152 and around the cervix 1154, when the uterus is contracted and the cervix temporarily dilates and shortens.

It is noted, and may be seen in FIGS. 12A and 12B, that a lower ring of an example embodiment of the device may be situated in the vagina, below the cervix and below the anchoring component.

Figure 13B:
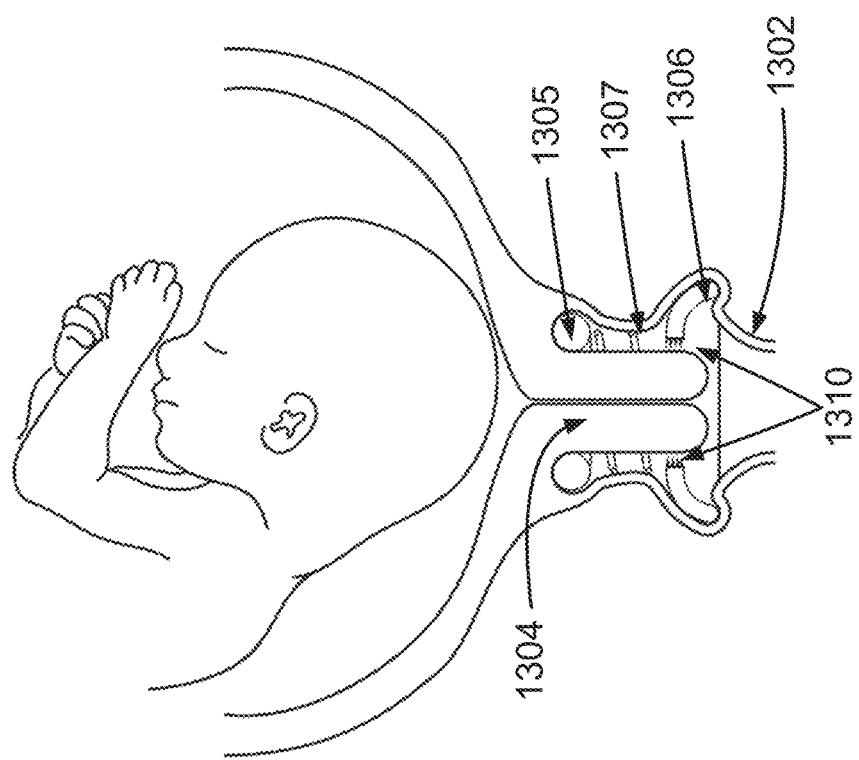
FIG. 13B is a simplified illustration of yet another example embodiment of the invention within a vagina and around a cervix.
Figure 13A:
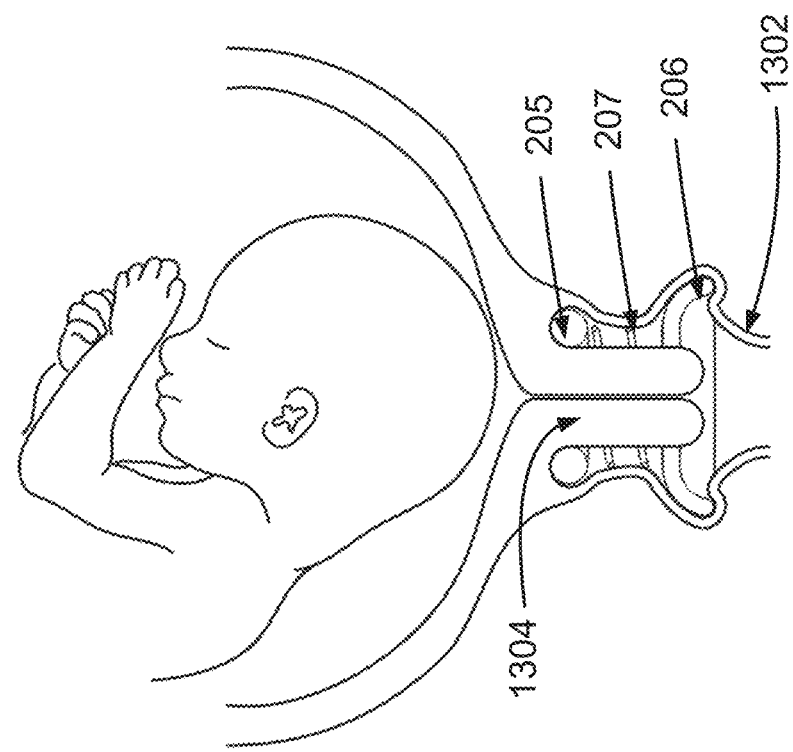
FIG. 13A is a simplified illustration of the example embodiment of FIG. 2A within a vagina and around a cervix.

Reference is now made to FIG. 13A, which is a simplified illustration of the example embodiment of FIG. 2A within a vagina 1302 and around a cervix 1304.

FIG. 13A depicts an upper ring 205 and a lower ring 206 connected to each other by an elastic component 207. The upper ring 205 is positioned high up on the cervix 1154, and the lower ring 206 is positioned to anchor against side walls of the vagina 1302.

Reference is now made to FIG. 13B, which is a simplified illustration of yet another example embodiment of the invention within a vagina 1302 and around a cervix 1304.

FIG. 13B depicts an upper ring 1305 and a lower ring 1306 connected to each other by an elastic component 1307. The upper ring 1305 is positioned high up on the cervix 1154, and the lower ring 1306 is positioned to anchor against side walls of the vagina 1302.

FIG. 13B depicts an example embodiment in which the lower ring 1306 additionally includes projections 1310 similar to the projections 806 shown in FIG. 8A. The projections 1310 potentially prevent the device from slipping off the cervix, and potentially anchor and/or assist anchoring the device in place.

Figure 14A:
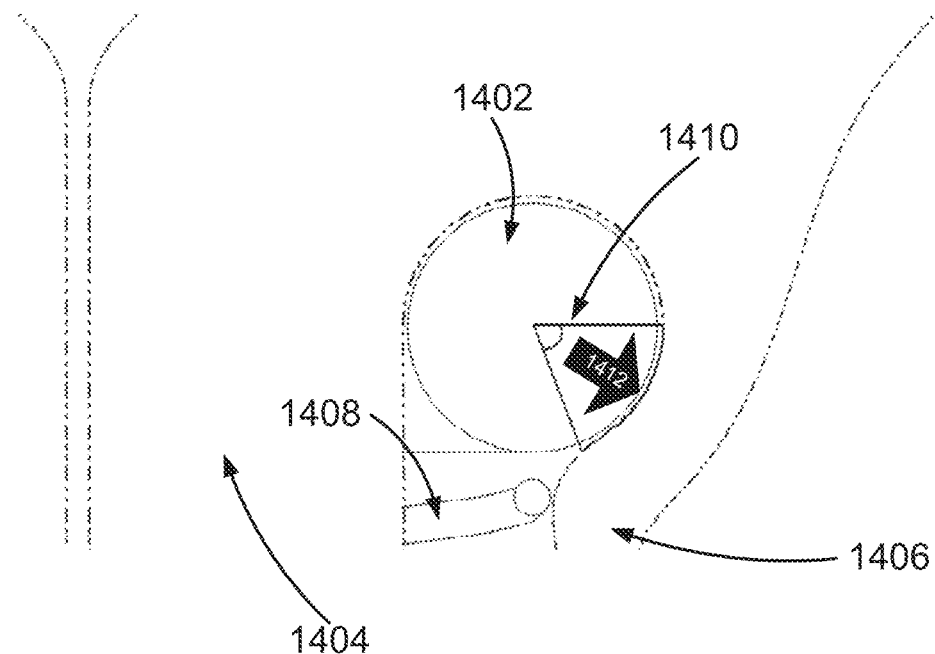
FIG. 14A is a simplified illustration of a force applied on a wall of the vagina by a device for delaying pre-term delivery according to an example embodiment of the invention.

Reference is now made to FIG. 14A, which is a simplified illustration of a force applied on a wall of the vagina by a device for delaying pre-term delivery according to an example embodiment of the invention.

FIG. 14A is a cross-sectional view of an upper ring 1402 in place contacting the fornix, around a cervix 1404, between the cervix 1404 and a wall of the vagina 1406. FIG. 14A also depicts a cross-section of an elastic component 1408 pushing the upper ring 1402 into place. A section 1410 of the upper ring 1402 which is pushing against a side wall of the vagina is depicted, pushing with a force 1412.

FIG. 14A depicts a reaction force by internal body organs pushing vaginal tissue around the device, potentially taking a shape surrounding the device. In some embodiments, by using a device shape which allows the tissue to collapse and even partially surround a bottom side of the device, one form of anchoring may be potentially be achieved.

The force 1412 is potentially proportional to a contact surface area between the upper ring 1402 and the surrounding tissue. The more contact surface area between the upper ring 1402 and the surrounding tissue, the larger the magnitude of a component of the force 1412 in a radial direction absorbed by the device instead of going in a direction which might potentially push the device out upon contraction of the uterus.

Figure 14B:
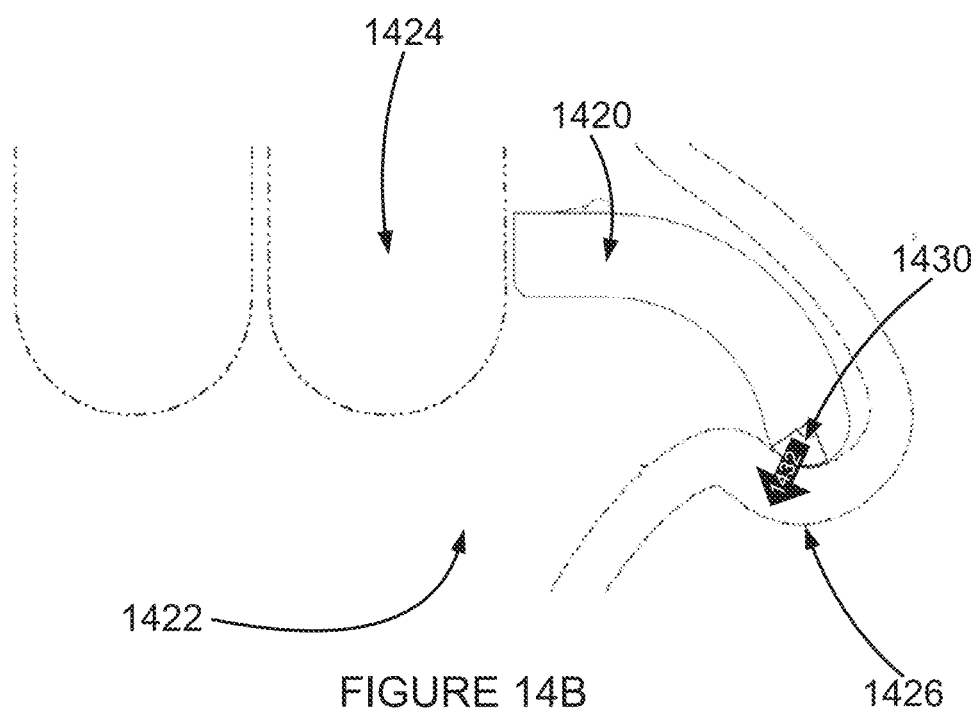
FIG. 14B is another simplified illustration of a force applied on a wall of the vagina by a device for delaying pre-term delivery according to an example embodiment of the invention.

Reference is now made to FIG. 14B, which is another simplified illustration of a force applied on a wall of the vagina by a device for delaying pre-term delivery according to an example embodiment of the invention.

FIG. 14B is a cross-sectional view of a lower ring anchoring component 1420 in place in a vagina 1422, between the cervix 1424 and a wall 1426 of the vagina 1422. A section 1430 of the anchoring component 1420 which is pushing against the wall 1426 of the vagina 1422 is depicted, pushing with a force 1432.

FIGS. 14A and 14B depict the vaginal wall's natural tendency to close in on itself, minimizing vagina volume, and potentially adding anchoring to the lower ring and/or to the upper ring.

FIGS. 14A and 14B depict that there is potentially a significant reaction force which may potentially anchor the device by the top ring or by the bottom ring or by both. As described above, the vaginal walls may potentially collapse on the device. The geometry of the device, by way of a non-limiting example including round shapes of the upper ring and lower ring, potentially enable the vaginal walls to collapse in a way which surrounds a part of the rings' surface area, and potentially provide full or partial anchoring.

Figure 15:
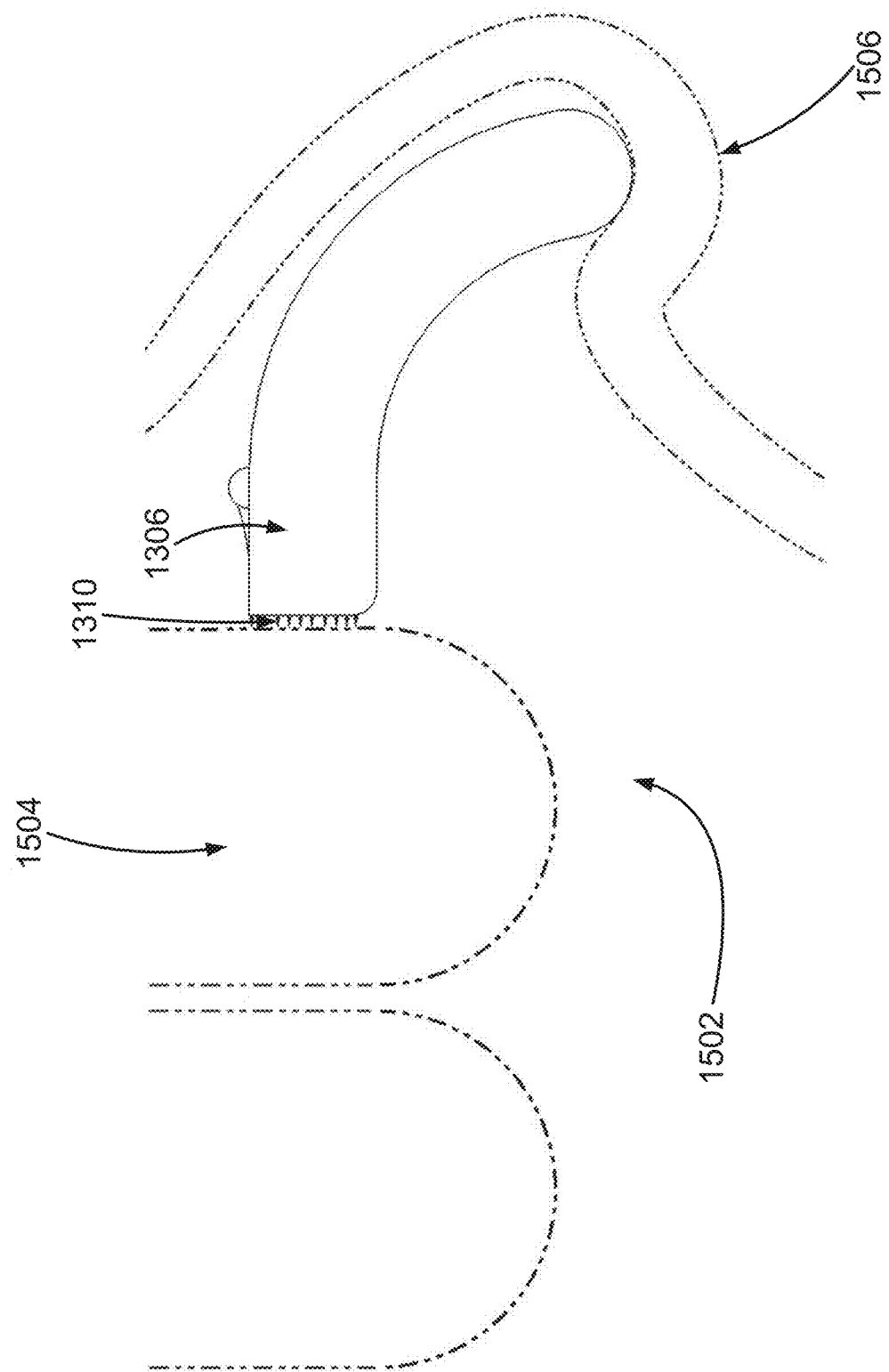
FIG. 15 is another simplified illustration of a force applied on a wall of the vagina by the device of FIG. 13B.

Reference is now made to FIG. 15, which is another simplified illustration of a force applied on a wall of the vagina by the device of FIG. 13B.

FIG. 15 depicts the lower ring 1306 positioned to anchor against a side wall 1506 of the vagina 1502.

FIG. 15 depicts the example embodiment in which the lower ring 1306 additionally includes projections 1310 similar to the projections 806 shown in FIG. 8A. The projections 1310 potentially prevent the device from slipping off the cervix 1504, and potentially anchor and/or assist anchoring the device in place.

It is expected that during the life of a patent maturing from this application many relevant tocolytic drugs will be developed and the scope of the term tocolytic drugs is intended to include all such new drugs a priori.

As used herein the term "about" refers to ±10%.

The terms "comprising", "including", "having" and their conjugates mean "including but not limited to".

The term "consisting of" is intended to mean "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a unit" or "at least one unit" may include a plurality of units, including combinations thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the engineering, chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of retarding birth comprising:
   placing a device for retarding birth on a cervix, the placing the device comprising:
   inserting the device into a vagina;
   placing a ring around the cervix, comprising:
      expanding the ring to be wider than the cervix;
      pushing the ring up along the cervix toward an upper portion of the cervix; and
      releasing the ring to grip the cervix; and
   placing an anchoring component around the cervix;
   such that when the upper portion of the cervix exerts force on the ring, the ring exerts an inward closing force on the anchoring component.

2. The method according to claim 1 and further including automatically releasing the device from the cervix.

3. The method according to claim 2 wherein the automatically releasing comprises automatically releasing the anchoring component from anchoring the device to the cervix based on a force of uterine contractions.

4. The method according to claim 2 wherein the automatically releasing comprises using a unit to activate automatic release of the device from the cervix based, at least in part, on force of contractions exceeding a known threshold.

5. The method according to claim 1 wherein the placing the anchoring component around the lower portion of the cervix comprises:
   expanding the anchoring component to be wider than the cervix; and
   releasing the anchoring component to grip the cervix.

6. The method of claim 1 and further comprising:
   activating a quick release mechanism to release an anchoring component from anchoring the device to a body of a patient.

7. The method of claim 1 and further comprising anchoring the anchoring component of the device against the cervix.

8. The method of claim 1 and further comprising:
   using a gauge arranged to indicate a force exerted upon the ring, thereby estimating a force exerted by a uterine contraction.

9. The method according to claim 1 and further comprising using a component arranged to indicate a birth progress parameter.

10. The method according to claim 1 and further comprising the device using a component to release a drug.

11. The method according to claim 1 and further comprising using a gauge attached to the device and reading a marking arranged to indicate a degree to which the anchoring component is compressed.

12. A device for retarding birth comprising:
the device having an internal cavity volume shaped as a lumen sized and shaped for surrounding a cervix;
longitudinal strips extending from an upper end of the lumen to an anchoring component;
the upper end of the lumen sized and shaped for surrounding the cervix; and
a ring surrounding the anchoring component and compressing the anchoring component toward a center of the lumen, wherein the ring is configured to be expanded to be wider than the cervix, pushed up along the cervix toward an upper portion of the cervix and released to grip the cervix,
the device configured such that when the upper portion of the cervix exerts force on the upper end of the lumen, the device enables a vector change of the exerted force such that the upper end exerts an inward closing force on the anchoring component.

13. The device of claim 12 wherein the anchoring component comprise a surface arranged so as to increase friction with a surface of the cervix when the surface of the anchoring component is located against the surface of the cervix so as to anchor against the cervix.

14. The device of claim 12 wherein the anchoring component is at a lower end of the lumen.

15. The device of claim 12 and further comprising an automatic release mechanism to release the anchoring component from anchoring the device to the cervix.

16. The device of claim 15 wherein the automatic release mechanism is configured to release the anchoring component from anchoring the device to the cervix based on a force of uterine contractions.

17. The device of claim 12 and further comprising a quick release mechanism to release the anchoring component from anchoring the device to the cervix.

18. The device of claim 12 and further comprising a component for measuring birth progress parameters.

19. The device of claim 12 and further comprising a component for releasing a drug.

20. The device of claim 12 in which a distance between the upper end of the lumen and the anchoring component is less than a length of a cervix.

21. The device of claim 12 and further comprising a gauge attached to the device and comprising a marking arranged to indicate a degree to which the anchoring component is compressed.

22. The device of claim 12 and further comprising a unit for measuring a force of contractions.

23. The device of claim 22 and further comprising a unit for activating automatic release of the device from the cervix based, at least in part, on the force of contractions exceeding a known threshold.

* * * * *